United States Patent
Andries et al.

(10) Patent No.: US 6,903,213 B2
(45) Date of Patent: Jun. 7, 2005

(54) HIV INHIBITING PYRIMIDINE DERIVATIVES

(76) Inventors: Koenraad Jozef Lodewijk Marcel Andries, Oosteneinde 9, B-2340 Beerse (BE); Bart De Corte, 1590 Winding Rd., Southampton, PA (US) 18966; Marc René De Jonge, Hontenissestraat 3, 5045 CA Tilburg (NL); Jan Heeres, Leemskuilen 18, B-2350 Vosselaar (BE); Chih Yung Ho, 600 Drinnon Way, Lansdale, PA (US) 19446; Marcel August Constant Janssen, Karel Druytslaan 15, B-2350 Vosselaar (BE); Paul Adriaan Jan Janssen, Antwerpsesteenweg 20, B-2350 Vosselaar (BE); Lucien Maria Henricus Koymans, Stationstraat 68 bus 4, B-2300 Turnhout (BE); Michael Joseph Kukla, 1551 Oak Hollow Dr., Maple Glen, PA (US) 19002; Donald William Ludovici, 1390 Masi Rd., Quarkertown, PA (US) 18951; Koen Jeanne Alfons Van Aken, Tuinbouwstraat 22, bus 2, B-2300 Turnhout (BE)

( * ) Notice: Subject to any disclaimer, the term of this patent is extended or adjusted under 35 U.S.C. 154(b) by 145 days.

(21) Appl. No.: 10/185,528

(22) Filed: Jun. 28, 2002

(65) Prior Publication Data

US 2003/0083317 A1 May 1, 2003

Related U.S. Application Data

(62) Division of application No. 09/749,181, filed on Dec. 27, 2000, now Pat. No. 6,440,986, which is a continuation of application No. 09/276,360, filed on Mar. 25, 1999, now Pat. No. 6,197,779.
(60) Provisional application No. 60/079,632, filed on Mar. 27, 1998.

(30) Foreign Application Priority Data

May 14, 1998 (EP) ............................................. 98201587
Nov. 25, 1998 (EP) ............................................. 98203948

(51) Int. Cl.$^7$ .......................................... D07D 239/42
(52) U.S. Cl. ................. 544/331; 544/320; 544/321; 544/323; 544/324; 544/330; 544/332
(58) Field of Search ................. 544/331, 314, 544/323, 324, 320, 321, 330, 332

(56) References Cited

U.S. PATENT DOCUMENTS

| 4,659,363 A | 4/1987 | Hubele et al. ............. 71/92 |
| 5,017,466 A | 5/1991 | Kobayashi et al. ......... 430/558 |

(Continued)

FOREIGN PATENT DOCUMENTS

| EP | 0 270 111 | 8/1988 |
| JP | 2308248 | 12/1990 |

(Continued)

OTHER PUBLICATIONS

Chen et al., J.Med. Chem., vol. 39, p. 4358–4360 1996.
D.Gosh et al., J. Med. Chem., 10(5), 974–5 (1967).
D. Gosh, J. Indian Chem. Soc., 58(5), 512–13 (1981).
Chem. Abstract 56:14278g; Shealy et al., J. Org. Chem. 26, 4433–40 (1961).
Chem. Abstract 64:5109h; Brit. 1,010,998.
Chem Abstract 65:2647d; Ghosh , J. Med. Chem. 9(3), 423–4 (1966).
Chem Abstract 71:89756n; Ghosh et al., FEBS Lett, 4(3), 157–9 (1969).
Chem Abstract 73:35322r;Arutyunyan et al., Izv. akad. Nauk SSSR, Sec. Khim (4)904–9 (1970).

(Continued)

Primary Examiner—Richard L. Raymond

(57) ABSTRACT

This invention concerns the use of the compounds of formula

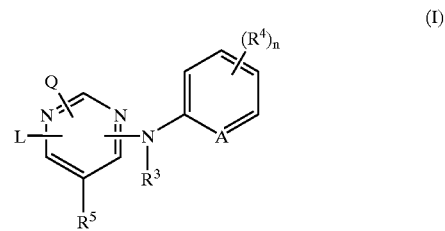

(I)

the N-oxides, the pharmaceutically acceptable addition salts and the stereochemically isomeric forms thereof, wherein A is CH, CR$^4$ or N; n is 0 to 4; Q is hydrogen or —NR$^1$R$^2$; R$^1$ and R$^2$ are selected from hydrogen, hydroxy, C$_{1-12}$alkyl, C$_{1-12}$alkyloxy, C$_{1-12}$alkylcarbonyl, C$_{1-12}$alkyloxycarbonyl, aryl, amino, mono- or di(C$_{1-12}$alkyl)-amino, mono- or di(C$_{1-12}$alkyl)aminocarbonyl wherein each C$_{1-12}$alkyl may optionally be substituted; or R$^1$ and R$^2$ taken together may form pyrrolidinyl, piperidinyl, morpholinyl, azido or mono- or di(C$_{1-12}$alkyl)aminoC$_{1-4}$alkylidene; R$^3$ is hydrogen, aryl, C$_{1-6}$alkylcarbonyl, optionally substituted C$_{1-6}$alkyl, C$_{16}$alkyloxy-carbonyl,; and R$^4$ is hydroxy, halo, optionally substituted C$_{1-6}$alkyl, C$_{1-6}$alkyloxy, cyano, aminocarbonyl, nitro, amino, trihalomethyl, trihalomethyloxy; R$^5$ is hydrogen or C$_{1-4}$alkyl; L is optionally substituted C$_{1-10}$alkyl, C$_{3-10}$alkenyl, C$_{3-10}$alkynyl, C$_{3-7}$cycloalkyl; or L is —X$^1$—R$^6$ or —X$^2$-Alk-R$^7$ wherein R$^6$ and R$^7$ are optionally substituted phenyl; X$^1$ and X$^2$ are —NR$^3$—, —NH—NH—, —N=N—, —O—, —S—, —S(=O)— or —S(=O)$_2$—; Alk is C$_{1-4}$alkanediyl; aryl is potionally substituted phenyl; Het is an optionally substituted aliphatic or aromatic heterocyclic radical; for the manufacture of a medicine for the treatment of subjects suffering from HIV (Human Immunodeficiency Virus) infection. It further relates to new compounds being a subgroup of the compounds of formula (I), their preparation and compositions comprising them.

1 Claim, No Drawings

U.S. PATENT DOCUMENTS

| | | |
|---|---|---|
| 5,516,775 A | 5/1996 | Zimmermann et al. .. 514/224.2 |
| 5,716,722 A | 2/1998 | Hamada et al. ............. 428/690 |
| 5,837,436 A | 11/1998 | Mihayashi et al. ......... 430/503 |

FOREIGN PATENT DOCUMENTS

| | | |
|---|---|---|
| JP | 4159381 | 6/1992 |
| JP | 8199163 | 8/1996 |
| JP | 9101590 | 4/1997 |
| JP | 2000111191 | 4/2000 |
| WO | WO 91/18887 | 12/1991 |
| WO | WO 94/02470 | 2/1994 |
| WO | 94/02470 | 2/1994 |
| WO | WO 95/10506 | 4/1995 |
| WO | WO 95/15952 | 6/1995 |
| WO | WO 97/ 19065 | 5/1997 |
| WO | 98/41512 | 9/1998 |

OTHER PUBLICATIONS

Chem Abstract 79:5309y: Harris et al., J. Heterocyclic CHem. 10(2), 167–71 (1973).

Chen Abstract 84:17272x; Sen et al., J. Indian. Chem., Soc. 52 (8), 774–5 (1975).

Chem. Abstract 116:633ot; Aoyagi et al., J. Heterocycl. Chem., 28 6) 1537–9 (1991).

Chem. Abstract 126:310419h; JP09068784, 1990.

Chem. Abstract 113:123850m: JP 02052360, 1990.

Chem. Abstract 114:230675a; JP 02300264, 1990.

Chem. Abstract 127:295356k; Deng et al., Huozhayaa, 20(3), 13 (1997).

Chem Abstract 86:6386; DE 2611826, Sep. 30, 1976.

Chem Abstract 88:38952; GB14773498, Jun. 22, 1977.

HIV INHIBITING PYRIMIDINE DERIVATIVES

This application is a divisional of prior application U.S. Ser. No. 09/749,181, filed Dec. 27, 2000, now U.S. Pat. No. 6,440,986, which is a continuation of prior application U.S. Ser. No. 09/276,360, filed Mar. 25, 1999, now issued as U.S. Pat. No. 6,197,779 B1, which claims priority from U.S. provisional application Ser. No. 60/079,632, filed Mar. 27, 1998, the contents of all of which are hereby incorporated by reference.

The present invention is concerned with pyrimidine derivatives having HIV replication inhibiting properties. The invention further relates to methods for their preparation and pharmaceutical compositions comprising them. The invention also relates to the use of said compounds in the manufacture of a medicament useful for the treatment of subjects suffenne from HIV (Human Immunodeficiency Virus) infection.

Compounds structurally related to the present compounds are disclosed in the prior art.

JP-2,052,360, JP-2,308,248, JP-9,080,676 and JP-9,068,784 disclose a number of trisubstituted pyrimidines useful in photographic material. JP-8,199,163 discloses trisubstituted pyrimidines useful in an organic electroluminescent device. JP-2,300,264 and GB-1,477,349 disclose pyrimidinetriamines for their use in the dye industry.

J. Indian Chem. Soc. (1975), 52(8), 774–775 discloses the synthesis of some bis(arylamino)pyrimidines. J. Heterocycl. Chem. (1973), 10(2), 167–171 discloses the condensation of various aminopyrimidines with picryl halides. J. Org. Chem. (1961), 26, 4433–4440 discloses several triaminopyrimidines as intermediates in the synthesis of triazolo[4,5-d]pyrimidines.

WO 91/18887 discloses diaminopyrimidines as gastric acid secretion inhibitors.

Unexpectedly, it has now been found that the compounds of formula (1) effectively inhibit the replication of the Human Immunodeficiency Virus (HIV) and consequently may be useful for the treatment of individuals infected by HIV.

The present invention concerns the use of the compounds of formula

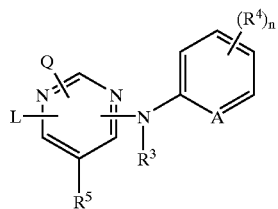

(I)

the N-oxides, the pharmaceutically acceptable addition salts and the stereochemically isomeric forms thereof, wherein A is CH, $CR^4$ or N;

n is 0, 1, 2, 3 or 4;

Q is hydrogen or $-NR^1R^2$;

$R^1$ and $R^2$ are each independently selected from hydrogen, hydroxy, $C_{1-12}$alkyl, $C_{1-12}$alkyloxy, $C_{1-12}$alkylcarbonyl, $C_{1-12}$alkyloxycarbonyl, aryl, amino, mono- or di($C_{1-12}$alkyl)amino, mono- or di($C_{1-12}$alkyl)aminocarbonyl wherein each of the aforementioned $C_{1-12}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, aminocarbonyl, aminocarbonylamino, mono- or di($C_{1-6}$alkyl)amino, aryl and Het; or $R^1$ and $R^2$ taken together may form pyrrolidinyl, piperidinyl, morpholinyl, azido or mono- or di($C_{1-12}$alkyl)amino$C_{1-4}$alkylidene;

$R^3$ is hydrogen, aryl, $C_{1-6}$alkylcarbonyl, $C_{1-6}$alkyl, $C_{1-6}$alkyloxycarbonyl, $C_{1-6}$alkyl substituted with $C_{1-6}$alkyloxycarbonyl; and each $R^4$ independently is hydroxy, halo, $C_{1-6}$alkyl, $C_{1-6}$alkyloxy, cyano, aminocarbonyl, nitro, amino, trihalomethyl, trihalomethyloxy or $C_{1-6}$alkyl substituted with cyano or aminocarbonyl;

$R^5$ is hydrogen or $C_{1-4}$alkyl;

L is $C_{1-10}$alkyl, $C_{3-10}$alkenyl, $C_{3-10}$alkynyl, $C_{3-7}$cycloalkyl, or $C_{1-10}$alkyl substituted with one or two substituents independently selected from $C_{3-7}$cycloalkyl, indanyl, indolyl and phenyl, wherein said phenyl, indanyl and indolyl may be substituted with one, two, three, four or where possible five substituents each independently selected from halo, hydroxy, $C_{1-6}$alkyl, $C_{1-6}$alkyloxy, cyano, aminocarbonyl, $C_{1-6}$alkyloxycarbonyl, formyl, nitro, amino, trihalomethyl, trihalomethyloxy and $C_{1-6}$alkylcarbonyl; or L is $-X^1-R^6$ or $-X^2$-Alk-$R^7$ wherein $R^6$ and $R^7$ each independently are phenyl or phenyl substituted with one, two, three, four or five substituents each independently selected from halo, hydroxy, $C_{1-6}$alkyl, $C_{1-6}$alkyloxy, $C_{1-6}$alkylcarbonyl, $C_{1-6}$alkyloxycarbonyl, formyl, cyano, aminocarbonyl, nitro, amino, trihalomethyloxy and trihalomethyl; and $X^1$ and $X^2$ are each independently $-NR^3-$, $-NH-NH-$, $-N=N-$, $-O-$, $-S-$, $-S(=O)-$ or $-S(=O)_2-$;

Alk is $C_{1-4}$alkanediyl;

aryl is phenyl or phenyl substituted with one, two, three, four or five substituents each independently selected from halo, $C_{1-6}$alkyl, $C_{1-6}$alkyloxy, cyano, nitro and trifluoromethyl;

Het is an aliphatic or aromatic heterocyclic radical: said aliphatic heterocyclic radical is selected from pyrrolidinyl, piperidinyl, homopiperidinyl, piperazinyl, morpholinyl, tetrahydrofuranyl and tetrahydrothienyl wherein each of said aliphatic heterocyclic radical may optionally be substituted with an oxo group; and said aromatic heterocyclic radical is selected from pyrrolyl, furanyl, thienyl, pyridyl, pyrimidinyl, pyrazinyl and pyridazinyl wherein each of said aromatic heterocyclic radical may optionally be substituted with hydroxy;

for the manufacture of a medicine for the treatment of subjects suffering from HIV (Human Immunodeficiency Virus) infection.

The present invention also relates to a method of treating warm-blooded animals suffering from HIV (Human Immunodeficiency Virus) infection. Said method comprises the administration of a therapeutically effective amount of a compound of formula (I) or any subgroup thereof, a N-oxide form, a pharmaceutically acceptable addition salt or a stereochemically isomeric form thereof in admixture with a pharmaceutical carrier.

This invention also concerns compounds of formula

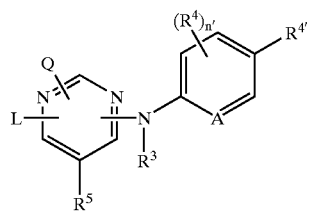

(I')

the N-oxides, the pharmaceutically acceptable addition salts and the stereochemically isomeric forms thereof, wherein L, Q, $R^3$, $R^4$, $R^5$ and A are as defined under formula (I), and $R^4$ is halo, $C_{1-6}$alkyl, cyano, aminocarbonyl, nitro, trihalomethyl, trihalomethyloxy or $C_{1-6}$alkyl substituted with cyano or aminocarbonyl;
n' is 0, 1, 2 or 3;
with the proviso that Q and L are other than anilino, 2,4,6-trinitro-anilino, 3-methoxy-anilino, 4-methoxy-anilino, 3,4-dimethoxy-anilino, 3-chloro-4-fluoro-anilino, 4-cyano-anilino, 2-($C_{1-6}$alkyl)-anilino, 4-($C_{1-6}$alkyl)-anilino, 3-chloro-anilino, 4-bromo-anilino, 4-nitro-anilino and 4-chloro-anilino.

As used in the foregoing definitions and hereinafter halo defines fluoro, chloro, bromo and iodo; $C_{1-4}$alkyl as a group or part of a group encompasses the straight and branched chained saturated hydrocarbon radicals having from 1 to 4 carbon atoms such as, for example, methyl, ethyl, propyl, butyl and the like; $C_{1-6}$alkyl as a group or part of a group encompasses the straight and branched chained saturated hydrocarbon radicals as defined in $C_{1-4}$alkyl as well as the higher homologues thereof containing 5 or 6 carbon atoms such as, for example pentyl or hexyl; $C_{1-10}$alkyl as a group or part of a group group encompasses the straight and branched chained saturated hydrocarbon radicals as defined in $C_{1-6}$alkyl as well as the higher homologues thereof containing 7 to 10 carbon atoms such as, for example, heptyl, octyl, nonyl or decyl; $C_{1-12}$alkyl as a group or part of a group encompasses the straight and branched chained saturated hydrocarbon radicals as defined in $C_{1-10}$alkyl as well as the higher homologues thereof containing 11 or 12 carbon atoms such as, for example, undecyl, dodecyl and the like; $C_{1-4}$alkylidene as a group or part of a group defines bivalent straight and branched chained hydrocarbons having from 1 to 4 carbon atoms such as, for example, methylene, ethylidene, propylidene, butylidene and the like; $C_{1-4}$alkanediyl as a group or part of a group encompasses those radicals defined under $C_{1-4}$alkylidene as well as other bivalent straight and branched chained hydrocarbons having from 1 to 4 carbon atoms such as, for example, 1,2-ethanediyl, 1,3-propanediyl, 1,4-butanediyl and the like. $C_{3-7}$cycloalkyl as a group or part of a group is generic to cyclopropyl, cyclobutyl, cyclopentyl, cyclohexyl and cycloheptyl: $C_{3-10}$alkenyl as a group or part of a group defines straight and branch chained hydrocarbon radicals containing one double bond and having from 3 to 10 carbon atoms such as, for example, 2-propenyl, 2-butenyl, 2-pentenyl, 3-pentenyl, 3-methyl-2-butenyl, 3-hexenyl, 3-heptenyl, 2-octenyl, 2-nonenyl, 2-decenyl and the like, whereby the carbon atom attached to the pyrimidine ring is preferably an aliphatic carbon atom; $C_{3-10}$alkynyl as a group or part of a group defines straight and branch chained hydrocarbon radicals containing one triple bond and having from 3 to 10 carbon atoms such as, for example, 2-propynyl, 2-butynyl, 2-pentynyl, 3-pentynyl, 3-methyl-2-butynyl, 3-hexynyl, 3-heptynyl, 2-octynyl, 2-nonynyl, 2-decynyl and the like, whereby the carbon atom attached to the pyrimidine ring is preferably an aliphatic carbon atom.

It is to be understood that the three substituents [L, Q and $NR^3$ (optionally substituted phenyl or pyridyl)] on the pyrimidine ring can be on any free position of the pyrimidine ring. Thus, given the following numbering of the pyrimidine ring

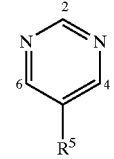

the three substituents may be connected to the pyrimidine ring in three different ways:
2-L, 4-Q, 6-$NR^3$ (optionally substituted phenyl or pyridyl); or
4-L, 2-Q, 6-$NR^3$ (optionally substituted phenyl or pyridyl); or
6-L, 4-Q, 2-$NR^3$ (optionally substituted phenyl or pyridyl).

The positions 4 and 6 are equivalent to one another. For instance, substitution pattern 6-L, 4-Q, 2-$NR^3$ (optionally substituted phenyl or pyridyl), which is a preferred substitution pattern, is equivalent to substitution pattern 4-L, 6-Q, 2-$NR^3$(optionally substituted phenyl or pyridyl). Said subgroup of compounds is represented by formula

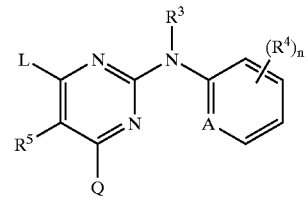

(I-1)

An interesting group of compounds are the compounds of formula

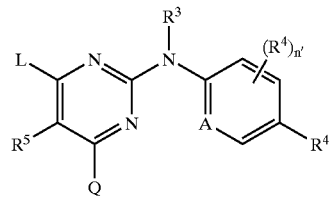

(I'-1)

Of particular interest are those compounds of formula (I'-1) wherein L and Q are other than anilino, 2,4,6-trinitro-anilino, 4-($C_{1-6}$alkyl)-anilino, 4-bromo-anilino, 4-nitro-anilino and 4-chloro-anilino: and of more particular interest are those compounds of formula (I'-1) wherein $R^{4'}$ is cyano, aminocarbonyl or $C_{1-6}$alkyl substituted with cyano or aminocarbonyl.

The addition salts as mentioned herein are meant to comprise the therapeutically active addition salt forms which the compounds of the present invention are able to form with appropriate acids, such as, for example, inorganic acids such as hydrohalic acids, e.g. hydrochloric or hydrobromic acid; sulfuric: nitric: phosphoric and the like acids: or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-amino-salicylic, pamoic and the like acids.

The pharmaceutically acceptable addition salts as mentioned hereinabove are also meant to comprise the therapeutically active non-toxic base, in particular, a metal or amine addition salt forms which the compounds of the present invention are able to form. Said salts can conveniently be obtained by treating the compounds of the present invention containing acidic hydrogen atoms with appropriate organic and inorganic bases such as, for example, the ammonium salts, the alkali and earth alkaline metal salts, e.g. the lithium, sodium, potassium, magnesium, calcium salts and the like, salts with organic bases. e.g. the benzathine, N-methyl-D-glucamine, hydrabamine salts, and salts with amino acids such as, for example, arginine, lysine and the like. Conversely said salt forms can be converted by treatment with an appropriate base or acid into the free acid or base form.

The term addition salts also comprises the hydrates and the solvent addition forms which the compounds of the present invention are able to form. Examples of such forms are e.g. hydrates, alcoholates and the like.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Some of the compounds of the present invention may also exist in their tautomeric forms. Such forms although not explicitly indicated in the above formula are intended to be included within the scope of the present invention.

Whenever used hereinafter, the term "compounds of the present invention" is meant to include the compounds of formula (I), (I-1), (I'), (I'-1) or any subgroup thereof, also the N-oxides, the pharmaceutically acceptable addition salts and all stereoisomeric forms.

The group containing those compounds of the present invention wherein Q is $NR^1R^2$, each $R^4$ independently is hydroxy, halo, $C_{1-6}$alkyl, $C_{1-6}$alkyloxy, cyano, aminocarbonyl, nitro, amino, trihalomethyl or trihalomethyloxy; L is $C_{1-10}$alkyl, $C_{3-10}$alkenyl, $C_{3-10}$alkynyl, $C_{3-7}$cycloalkyl, or $C_{1-10}$alkyl substituted with one or two substituents independently selected from $C_{3-7}$cycloalkyl, indolyl or indolyl substituted with one, two, three or four substituents each independently selected from halo, $C_{1-6}$alkyl, $C_{1-6}$alkyloxy, cyano, aminocarbonyl, nitro, amino, trihalomethyl, trihalomethyloxy and $C_{1-6}$alkylcarbonyl, phenyl or phenyl substituted with one, two, three, four or five substituents each independently selected from halo, hydroxy, $C_{1-6}$alkyl, $C_{1-6}$alkyloxy, cyano, aminocarbonyl, nitro, amino, trihalomethyl, trihalomethyloxy and $C_{1-6}$alkylcarbonyl; or L is —$X^1$—$R^6$ wherein $R^6$ is phenyl or phenyl substituted with one, two, three, four or five substituents each independently selected from halo, $C_{1-6}$alkyl, $C_{1-6}$alkyloxy, $C_{1-6}$alkylcarbonyl, cyano, nitro and trifluoromethyl; is of interest.

Also of interest is the group containing those compounds of the present invention wherein Q is $NR^1R^2$; each $R^4$ independently is hydroxy, halo, $C_{1-6}$alkyl, $C_{1-6}$alkyloxy, cyano, aminocarbonyl, nitro, amino, trihalomethyl or trihalomethyloxy ; L is $C_{1-10}$alkyl substituted with one or two substituents independently selected from phenyl or phenyl substituted with one, two, three, four or five substituents each independently selected from halo, hydroxy, $C_{1-6}$alkyl, $C_{1-6}$alkyloxy, cyano, aminocarbonyl, nitro, amino, trihalomethyl, trihalomethyloxy and $C_{1-6}$alkylcarbonyl; or L is —$X^1$—$R^6$ wherein $R^6$ is phenyl or phenyl substituted with one, two, three, four or five substituents each independently selected from halo, $C_{1-6}$alkyl, $C_{1-6}$alkyloxy, $C_{1-6}$alkylcarbonyl, cyano, nitro and trifluoromethyl; with the proviso that compounds (a) N2-hydroxy-N2-methyl-N4,N6-diphenyl-2,4,6-pyrimidinetriamine;
(b) N,N,N',N',N",N"-hexakis(3-methylphenyl)-2,4,6-pyrimidinetriamine;
(c) N4-methyl-N2-(2-methylphenyl)-N4-phenyl-2,4,6-pyrimidinetriamine;
(d) N4-methyl-N2-(2-methylphenyl)-N4-phenyl-6-(phenylmethyl)-2,4-pyrimidine diamine;
(e) N4-(2-methylphenyl)-6-(phenylmethyl)-2,4-pyrimidinediamine;
(f) N,N',N"-tris(4-methoxyphenyl)-2,4,6-pyrimidinetriamine;
(g) N,N'-bis(4-hexylphenyl)-6-(4-methoxyphenoxy)-2,4-pyrimidinediamine;
(h) N2,N4-bis(4-hexylphenyl)-N6,N6-dimethyl-2,4,6-pyrimidinetriamine;
(i) N,N',N"-tris(4-hexylphenyl)-2,4,6-pyrimidinetriamine;
(j) N2,N2-dimethyl-N4,N6-bis(4-methylphenyl)-2,4,6-pyrimidinetriamine;
(k) N,N',N"-tris(4-methylphenyl)-2,4,6-pyrimidinetriamine;
(l) N,N',N"-triphenyl-2,4,6-pyrimidinetriamine;
(m) N,N,N',N',N",N"-hexakis(4-ethoxyphenyl)-2,4,6-pyrimidinetriamine;
(n) N4,N6-bis(2-chlorophenyl)-2,4,6-pyrimidinetriamine;
(o) N4,N6-bis(3-chlorophenyl)-2,4,6-pyrimidinetriamine;
(p) N4,N6-bis(2-ethoxyphenyl)-2,4,6-pyrimidinetriamine;
(q) N4,N6-bis(4-ethoxyphenyl)-2,4,6-pyrimidinetriamine;
(r) N4,N6-bis(2-methylphenyl)-2,4,6-pyrimidinetriamine;
(s) N4,N6-bis(4-bromophenyl)-2,4,6-pyrimidinetriamine;
(t) N4,N6-bis(4-methylphenyl)-2,4,6-pyrimidinetriamine;
(u) N2,N4-bis(4-methoxyphenyl)-2,4,6-pyrimidinetriamine;
(v) N2,N4-bis(4-methylphenyl)-2,4,6-pyrimidinetriamine;
(w) N,N',N"-tris(2,4,6-trinitrophenyl)-2,4,6-pyrimidinetriamine;
(x) N4,N6-6-bis(4-chlorophenyl)-2,4,6-pyrimidinetriamine;
(y) N4,N6-bis(4-methoxyphenyl)-2,4,6-pyrimidinetriamine;
(z) N2,N4,N6-trimethyl-N2,N4,N6-triphenyl pyrimidine-2,4,6-triyltriamine;
(aa) N4,N4-dimethyl-N2,N6-di-p-tolyl-pyrimidine-2,4,6-triyltriamine; and
(bb) N2,N4-diphenyl-pyrimidine-2,4,6-triyltriamine are not included.

Suitably, Q may also be hydrogen in the above two groups of interest.

A special group of compounds are those compounds of formula (I) or (I') wherein n is at least 1 and at least one $R^4$ is cyano; preferably, n is 1 and $R^4$ is cyano substituted in the para position relative to the $NR^3$ moiety.

Another special group of compounds contains those compounds of formula (I) or (I') which are other than (c) N4-methyl-N2-(2-methylphenyl)-N4-phenyl-2,4,6-pyrimidinetriamine;

(d) N4-methyl-N2-(2-methylphenyl)-N4-phenyl-6-(phenylmethyl)-2,4-pyrimidinediamine;

(e) N4-(2-methylphenyl)-6-(phenylmethyl)-2,4-pyrimidinediamine; the N-oxides, the pharmaceutically acceptable addition salts and the stereochemically isomeric forms thereof.

An interesting group of compounds are those compounds of the present invention wherein the $NR^3$ (substituted phenyl or pyridyl) moiety is in the 4- or 6-position of the pyrimidine ring.

Another interesting group are those compounds of the present invention wherein each $R^4$ independently is hydroxy, halo, $C_{1-6}$alkyloxy, cyano, aminocarbonyl, nitro, amino, trihalomethyl or trihalomethyloxy; $R^6$ is phenyl or phenyl substituted with one, two or three, four or five substituents each independently selected from halo, $C_{1-6}$alkyloxy, $C_{1-6}$alkylcarbonyl, cyano, nitro and trifluoromethyl; and aryl is phenyl or phenyl substituted with one, two, three, four or five substituents each independently selected from halo, $C_{1-6}$alkyloxy, cyano, nitro and trifluoromethyl.

Suitably, Q is $NR^1R^2$ wherein $R^1$ is hydrogen, hydroxy, $C_{1-12}$alkyl, $C_{1-12}$alkyloxy, $C_{1-12}$alkylcarbonyl, $C_{1-12}$alkyloxycarbonyl, aryl, amino, mono- or di($C_{1-12}$alkyl)amino, mono- or di($C_{1-12}$alkyl)aminocarbonyl; and $R^2$ is hydroxy, $C_{1-12}$alkyl, $C_{1-12}$alkyloxy, $C_{1-12}$alkylcarbonyl, $C_{1-12}$alkyloxycarbonyl, aryl, amino, mono- or di($C_{1-12}$alkyl)amino, mono- or di($C_{1-12}$alkyl)aminocarbonyl; wherein each of the aforementioned $C_{1-12}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, aminocarbonyl, aminocarbonylamino, mono- or di($C_{1-6}$alkyl)amino, aryl and Het: or $R^1$ and $R^2$ taken together may form pyrrolidinyl, piperidinyl, morpholinyl, azido or mono- or di($C_{1-12}$alkyl)amino-$C_{1-4}$alkylidene.

Suitably, L is $C_{1-10}$alkyl substituted with one or two substituents independently selected from $C_{3-7}$cycloalkyl, indanyl, indolyl and phenyl, wherein said phenyl, indanyl and indolyl may be substituted with one, two, three, four or where possible five substituents each independently selected from halo, hydroxy, $C_{1-6}$alkyl, $C_{1-6}$alkyloxy, cyano, aminocarbonyl, $C_{1-6}$alkyloxycarbonyl, formyl, nitro, amino, trihalomethyl, trihalomethyloxy and $C_{1-6}$alkylcarbonyl; or L is —$X^1$-$R^6$ or —$X^2$-Alk-$R^7$ and when $X^1$ is $NR^3$, then $R^6$ is phenyl substituted with one, two, three, four or five substituents each independently selected from $C_{1-6}$alkyloxycarbonyl, formyl, nitro and trihalomethyloxy.

Suitably, $R^4$ or $R^{4'}$ is nitro, trihalomethyloxy or $C_{1-6}$alkyl substituted with cyano or aminocarbonyl.

Suitably, $R^6$ is phenyl or phenyl substituted with one, two, three, four or five substituents each independently selected from halo, hydroxy, $C_{1-6}$alkyl, $C_{1-6}$alkyloxy, $C_{1-6}$alkyloxycarbonyl, formyl, cyano, aminocarbonyl, nitro, amino, trihalomethyloxy and trihalomethyl.

Suitably, both Q and $R^5$ are hydrogen.

Suitably, L is $C_{1-10}$alkyl substituted with one or two substituents independently selected from $C_{3-7}$cycloalkyl, indanyl, indolyl and phenyl, wherein said phenyl, indanyl and indolyl may be substituted with one, two, three, four or where possible five substituents each independently selected from halo, hydroxy, $C_{1-6}$alkyl, $C_{1-6}$alkyloxy, cyano, aminocarbonyl, $C_{1-6}$alkyloxycarbonyl, formyl, nitro, amino, trihalomethyl, trihalomethyloxy and $C_{1-6}$alkylcarbonyl; or L is —$X^1$-$R^6$ or —$X^2$-Alk-$R^7$; and $R^5$ is hydrogen.

Particular groups of compounds are those groups wherein one or more of the following conditions are met:

(i) n is 0, 1, 2 or 3;

(ii) Q is hydrogen;

(iii) Q is $NR^1R^2$ wherein $R^1$ and $R^2$ are each independently selected from hydrogen, hydroxy, $C_{1-12}$alkyl $C_{1-12}$alkyloxy $C_{1-12}$alkylcarbonyl, $C_{1-12}$alkyloxycarbonyl, cyano wherein the aforementioned $C_{1-12}$alkyl groups may optionally and each individually be substituted with one or two substituents each independently selected from hydroxy, cyano, $C_{1-6}$alkyloxy, hydroxy$C_{1-6}$alkyloxy, aryl and Het; or $R^1$ and $R^2$ taken together may form mono- or di($C_{1-12}$alkyl)amino$C_{1-4}$alkylidene;

(iv) $R^3$ is hydrogen or $C_{1-6}$alkyl;

(v) $R^4$ is cyano, aminocarbonyl, amino, nitro, hydroxy, halo, $C_{1-6}$alkyl or cyano$C_{1-6}$alkyl;

(vi) $R^4$ is cyano, aminocarbonyl, halo, $C_{1-6}$alkyl or cyano$C_{1-6}$alkyl;

(vii) $R^5$ is hydrogen or methyl;

(viii) L is $C_{1-10}$alkyl substituted with phenyl substituted with one or two halogens; or L is —$X^1$—$R^6$ wherein $R^6$ is phenyl substituted with one, two or three substituents selected from $C_{1-6}$alkyl, trifluoromethyl, trifluoromethoxy, cyano, and halogen, and $X^1$ is —S—, —O— or —$NR^3$—; or L is —$X^2$-Alk-$R^7$— wherein $R^7$ is phenyl substituted with one, two or three substituents selected from $C_{1-6}$alkyl, cyano, and halogen and $X^2$ is NH.

Other particular compounds are those compounds of the present invention wherein L contains phenyl, 2,6-disubstituted-phenyl, 2,4,6-trisubstituted-phenyl or 2,3,4,5-tetra-substituted-phenyl;

especially, L contains phenyl, 2,4,6-trihalo-phenyl, 2,4,6-tri$C_{1-4}$alkyl-phenyl, 2,3,4,5-tetrahalo-phenyl, 2,4-dihalo-6-$C_{1-4}$alkyl-phenyl, 2,6-dihalo-4-$C_{1-4}$alkyl-phenyl, 2,6-dihalo-4-cyano-phenyl, 2,6-dihalo-4-trifluoromethoxy-phenyl, 2,6-dihalo-4-trifluoromethyl-phenyl, 2,6-di$C_{1-4}$alkyl-4-halo-phenyl, 2,6-di$C_{1-4}$alkyl-4-cyano-phenyl, 2,6-dihalo-phenyl or 2,6-di$C_{1-4}$alkyl-phenyl;

more in particular, L contains phenyl, 2,4,6-trichlorophenyl, 2,4,6-trimethyl-phenyl, 2,4-dibromo-3,5-dichloro-phenyl, 2,4-dibromo-6-fluoro-phenyl, 2,4-dichloro-6-methyl-phenyl, 2,6-dibromo-4-isopropyl-phenyl, 2,6-dibromo-4-methyl-phenyl, 2,6-dibromo-4-prop-1-yl-phenyl, 2,6-dichloro-4-cyano-phenyl, 2,6-dichloro-4-trifluoromethoxy-phenyl, 2,6-dichloro-4-trifluoromethyl-phenyl, 2,6-dichloro-phenyl, 2,6-dimethyl-4-(1,1-dimethylethyl)-phenyl, 2,6-dimethyl-phenyl, 2-bromo-4-fluoro-6-methyl-phenyl, 2-bromo-6-chloro-4-fluoro-phenyl, 4-bromo-2,6-dimethyl-phenyl, 4-chloro-2,6-dimethyl-phenyl, or 4-cyano-2,6-dimethyl-phenyl.

More particular compounds are the compounds of the present invention wherein L is 2,6-dichlorobenzyl, or L is —$X^1$—$R^6$ wherein $X^1$ is —$NR^3$—, —S— or —O— and $R^6$ is 2,4,6-trichlorophenyl, 2,4,6-trimethyl-phenyl, 2,4-dibromo-3,5-dichloro-phenyl, 2,4-dibromo-6-fluoro-phenyl, 2,4-dichloro-6-methyl-phenyl, 2,6-dibromo-4-isopropyl-phenyl, 2,6-dibromo-4-methyl-phenyl, 2,6-dibromo-4-prop-1-yl-phenyl, 2,6-dichloro-4-cyano-phenyl, 2,6-dichloro-4-trifluoromethoxy-phenyl, 2,6-dichloro-4-trifluoromethyl-phenyl, 2,6-dichloro-phenyl, 2,6-dimethyl-4-(1,1-dimethylethyl)-phenyl, 2,6-dimethyl-phenyl, 2-bromo-4-fluoro-6-methyl-phenyl, 2-bromo-6-chloro-4-fluoro-phenyl, 4-bromo-2,6-dimethyl-phenyl 4-chloro-2,6-dimethyl-phenyl, 4-cyano-2,6-dimethyl-phenyl; or L is —$X^2$-Alk-$R^7$ wherein —$X^2$-Alk- is —NH—$CH_2$— and $R^7$ phenyl.

Still other particular compounds are those compounds of formula (I) where $R^3$ is hydrogen, A is CH, n is 1, and $R^4$ is halo, methyl or cyano and is positioned in the 4 position of the phenyl ring.

Preferred compounds are those compounds of the present invention wherein L is 2,6-dichlorobenzyl and the $NR^3$ (optionally substituted phenyl or pyridyl) moiety represents p-cyano-anilino and is in the 2 position of the pyrimidine ring.

Other preferred compounds are those compounds of the present invention wherein Q is hydrogen. L is —$X^1$—$R^6$ wherein $X^1$ is —NH— and $R^6$ is 2,4,6-trimethyl-phenyl or 4-cyano-2,6-dimethylphenyl, the $NR^3$ (optionally substituted phenyl or pyridyl) moiety represents p-cyano-anilino and is in the 2 position of the pyrimidine ring.

Still other preferred compounds are those compounds of the present invention wherein L is —$X^2$-Alk-$R^7$ wherein $X^2$ is —NH—, Alk is methylene and $R^7$ is phenyl, 2,6-dichloro-phenyl, 2,4,6-trimethyl-phenyl or 4-cyano-2,6-dimethylphenyl.

More preferred are those compounds of formula (I'-1) wherein $R^{4''}$ is halo, cyano, aminocarbonyl or cyano$C_{1-6}$alkyl; n is zero, A is CH, $R^3$ is hydrogen; $R^5$ is hydrogen or methyl; Q is hydrogen or $NHR^1$; and L contains phenyl, 2,4,6-trichloro-phenyl, 2,4,6-trimethyl-phenyl, 2,4-dibromo-3,5-dichloro-phenyl, 2,4-dibromo-6-fluoro-phenyl, 2,4-dichloro-6-methyl-phenyl, 2,6-dibromo-4-isopropyl-phenyl, 2,6-dibromo-4-methyl-phenyl, 2,6-dibromo-4-prop-1-yl-phenyl, 2,6-dichloro-4-cyano-phenyl, 2,6-dichloro-4-trifluoromethoxy-phenyl, 2,6-dichloro-4-trifluoromethyl-phenyl, 2,6-dichloro-phenyl, 2,6-dimethyl-4-(1,1-dimethylethyl)-phenyl, 2,6-dimethyl-phenyl, 2-bromo-4-fluoro-6-methyl-phenyl, 2-bromo-6-chloro-4-fluoro-phenyl, 4-bromo-2,6-dimethyl-phenyl, 4-chloro-2,6-dimethyl-phenyl, or 4-cyano-2,6-dimethyl-phenyl.

Most preferred are
4-[[4-amino-6-[(2,6-dichlorophenyl)methyl]-2-pyrimidinyl]amino]benzonitrile;
6-[(2,6-dichlorophenyl)methyl]-N2-(4-fluorophenyl)-2,4-pyrimidinediamine;
4-[[4-[(2,4-dichlorophenyl)methyl]-6-[(4-hydroxybutyl)amino]-2-pyrimidinyl]amino]-benzonitrile;
4-[[4-[(2,6-dichlorophenyl)methyl]-6-[(3-hydroxypropyl)amino]-2-pyrimidinyl]amino]-benzonitrile;
N-[2-[(4-cyanophenyl)amino]-6-[(2,6-dichlorophenyl)methyl]-4-pyrimidinyl]-acetamide;
N-[2-[(4-cyanophenyl)amino]-6-[(2,6-dichlorophenyl)methyl]-4-pyrimidinyl]-butanamide;
4-[[2-amino-6-(2,6-dichlorophenoxy)-4-pyrimidinyl]amino]benzonitrile;
4-[[4-[(2,6-dichlorophenyl)methyl]-6-[(2-hydroxy-2-phenylethyl)amino]-2-pyrimidinyl]amino]benzonitrile;
4-[[4-[(2,6-dichlorophenyl)methyl]-6-[[3-(2-oxo-1-pyrrolidinyl)propyl]amino]-2-pyrimidinyl]amino]benzonitrile;
4-[[4-[(2,6-dichlorophenyl)methyl]-6-[[2-(2-hydroxyethoxy)ethyl]amino]-2-pyrimidinyl]amino]benzonitrile monohydrochloride;
4-[[4-[(2,6-dichlorophenyl)methyl]-6-[(2,3-dihydroxypropyl)amino]-2-pyrimidinyl]-amino]benzonitrile;
4-[[4-[(2,6-dichlorophenyl)methyl]-6-(hydroxyamino)-2-pyrimidinyl]amino]-benzonitrile;
4-[[4-[(2-cyanoethyl)amino]-6-[(2,6-dichlorophenyl)methyl]-2-pyrimidinyl]amino]-benzonitrile;
4-[[4-[(2,6-dichlorophenyl)methyl]-6-[[2-(1-pyrrolidinyl)ethyl]amino]-2-pyrimidinyl]-amino]benzonitrile;
4-[[4-amino-6-[(2,6-dichlorophenyl)methyl]-5-methyl-2-pyrimidinyl]amino]-benzonitrile;
N2-(4-bromophenyl)-6-[(2,6-dichlorophenyl)methyl]-5-methyl-2,4-pyrimidinediamine;
4-[[4-[(2,4,6-trimethylphenyl)amino]-2-pyrimidinyl]amino]benzonitrile;
4-[[2-[(2,4,6-trimethylphenyl)amino]-4-pyrimidinyl]amino]benzonitrile;
4-[[4-[(2,6-dimethylphenyl)amino]-2-pyrimidinyl]amino]benzonitrile;
4-[[4-(2,4,6-trimethylphenoxy)-2-pyrimidinyl]amino]benzonitrile;
4-[[4-[(2,6-dichlorophenyl)thio]-2-pyrimidinyl]amino]benzonitrile;
4-[[4-[[2,6-dibromo-4-(1-methylethyl)phenyl]amino]-2-pyrimidinyl]amino]-benzonitrile;
4-[[4-[[2,6-dichloro-4-(trifluoromethyl)phenyl]amino]-2-pyrimidinyl]amino]-benzonitrile;
4-[[4-[(2,4-dichloro-6-methylphenyl)amino]-2-pyrimidinyl]amino]benzonitrile;
4-[[2-[(cyanophenyl)amino]-4-pyrimidinyl]amino]-3,5-dimethylbenzonitrile;
4-[[4-[(2,4-dibromo-6-fluorophenyl)amino]-2-pyrimidinyl]amino]benzonitrile;
4-[[4-amino-6-[(2,6-dichlorophenyl)methyl]-5-methyl-2-pyrimidinyl]amino]-benzeneacetonitril
4-[[4-[methyl(2,4,6-trimethylphenyl)amino]-2-pyrimidinyl]amino]benzonitrile;
4-[[4-[(2,4,6-trichlorophenyl)amino]-2-pyrimidinyl]amino]benzonitrile;
4-[[4-[(2,4,6-trimethylphenyl)thio]-2-pyrimidinyl]amino]benzonitrile;
4-[[4-[(2,4,6-trimethylphenyl)amino-2-pyrimidinyl]amino]benzonitrile;
4-[[4-amino-6-[(2,4,6-trimethylphenyl)amino]-2-pyrimidinyl]amino]benzonitrile;
4-[[2-amino-6-[(2,4,6-trimethylphenyl)amino]-4-pyrimidinyl]amino]benzonitrile;
4-[[4-(2-bromo-4-chloro-6-methylphenoxy)-2-pyrimidinyl]amino]benzonitrile;
4-[[4-[(4-chloro-2,6-dimethylphenyl)amino]-2-pyrimidinyl]amino]benzonitrile;
3,5-dichloro-4-[[2-[(4-cyanophenyl)amino]-4-pyrimidinyl]amino]benzonitrile;
4-[[4-[[2,6-dichloro-4-(trifluoromethoxy)phenyl]amino]-2-pyrimidinyl]amino]-benzonitrile;
4-[[4-[(2,4-dibromo-3,6-dichlorophenyl)amino]-2-pyrimidinyl]amino]benzonitrile;
4-[[4-[(2,6-dibromo-4-propylphenyl)amino]-2-pyrimidinyl]amino]benzonitrile;
4-[[4-[(2,4,6-trimethylphenyl)amino]-2-pyrimidinyl]amino]benzamide;
4-[[4-[(4-(1,1-dimethylethyl)-2,6-dimethylphenyl)amino]-2-pyrimidinyl]amino]-benzonitrile;
4-[[2-[(4-cyanophenyl)amino]-4-pyrimidinyl]oxy]-3,5-dimethylbenzonitrile;
4-[[4-[(4-chloro-2,6-dimethylphenyl)amino]-5-methyl-2-pyrimidinyl]amino]-benzonitrile;
4-[[2-[(4-cyanophenyl)amino]-5-methyl-4-pyrimidinyl]amino-3,5-dimethyl-benzonitrile;
4-[[4-[[4-(1,1-dimethylethyl)-2,6-dimethylphenyl]amino]-5-methyl-2-pyrimidinyl]-amino]benzonitrile;
4-[[4-[(4-bromo-2,6-dimethylphenyl)amino]-5-methyl-2-pyrimidinyl]amino]-benzonitrile;
4-[[5-methyl-4-[(2,4,6-trimethylphenyl)thio]-2-pyrimidinyl]amino]benzonitrile;
4-[[4-[(2,6-dibromo-4-propylphenyl)amino]-5-methyl-2-pyrimidinyl]amino]-benzonitrile;

4-[[4-[(2,4,6-trimethylphenyl)amino]-2-pyrimidinyl]amino] benzamide, N3-oxide;

N2-(4-chlorophenyl)-N4-(2,4,6-trimethylphenyl)-2,4-pyrimidinediamine;

4-[[4-[[2,6-dibromo-4-(1-methylethyl)phenyl]amino]-5-methyl-2-pyrimidinyl]amino]-benzonitrile;

4-[[2-[(4-cyanophenyl)amino]-5-methyl-4-pyrimidinyl] amino]-3,5-dimethyl benzonitrile;

4-[[4-[(phenylmethyl)amino]-2-pyrimidinyl]amino] benzonitrile;

the N-oxides, the pharmaceutically acceptable addition salts and the stereochemically isomeric forms thereof.

The compounds of formula (I) can be prepared according to art-known procedures.

In particular, compounds of formula (I') can generally be prepared by reacting an intermediate of formula (II-A) wherein $W^1$ is a suitable leaving group such as, for example, a halogen, with an amino derivative of formula (III) optionally in a solvent such as, for example, water, 2-propanol, diethylether, 1-methyl-2-pyrrolidinone and the like, and optionally in the presence of an acid such as, for example, 1 N hydrochloric acid in diethylether. It may be convenient to perform the reaction under a reaction-inert atmosphere such as, for example, oxygen free argon or nitrogen.

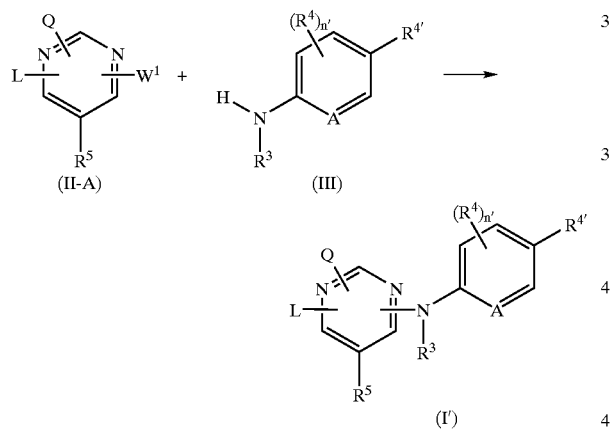

In this and the following preparations, the reaction products may be isolated from the reaction medium and, if necessary, further purified according to methodologies generally known in the art such as, for example, extraction, crystallization, distillation, trituration and chromatography.

Analogously to the reaction procedure described above, H—NR$^1$R$^2$ (VI) can also be reacted with an intermediate of formula (II-B).

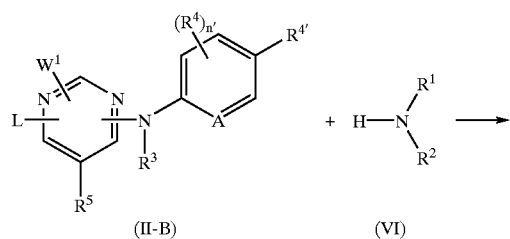

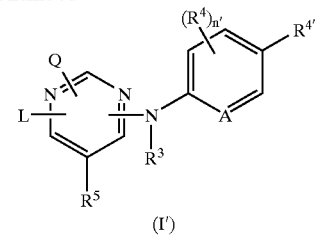

Suitable solvents for the above reaction include, for instance, 2-propanol or 1,4-dioxane.

In case Q is $NR^1R^2$ and $R^2$ contains a hydroxy moiety, it may be convenient to perform the above reaction with a protected form of intermediate (VI) whereby the hydroxy moiety bears a suitable protecting group P being, for instance, a benzyl, and subsequently removing the protective group according to art-known methodologies, such as, for example, reacting with BBr$_3$ in dichloromethane under nitrogen atmosphere.

It is also possible to react H—$X^1$—$R^6$ with an intermediate of formula (II-C) in a suitable solvent such as, for example, 1,4-dioxane, thus obtaining compounds of formula (I') wherein L is —$X^1$—$R^6$, said compounds being represented by formula (I'-c).

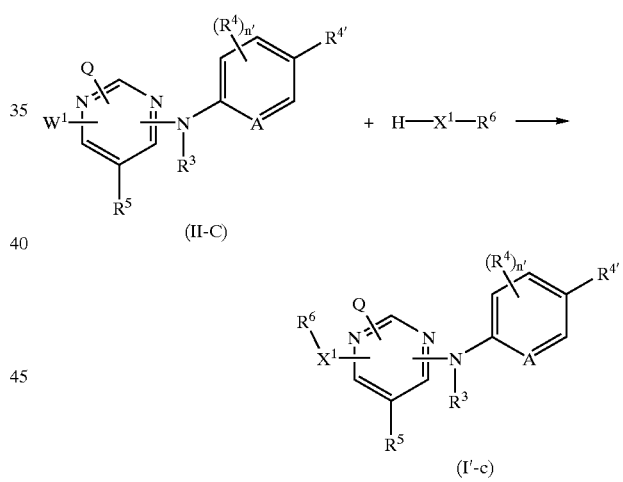

Depending on the nature of $X^1$ a suitable base or acid may be used to improve the reaction rate. For instance, in case $X^1$ is —O—, sodium hydride may be used as suitable base; or in case $X^1$ is $NR^3$, HCl may be used as a suitable acid.

The compounds of formula (I') may further be prepared by converting compounds of formula (I') into each other according to art-known group transformation reactions.

For instance, compounds of formula (I') whereby Q is $NR^1R^2$ and $R^1$ and $R^2$ are taken together to form mono- or di($C_{1-12}$alkyl)amino$C_{1-4}$alkylidene, said compounds being represented by formula (I'-a), may be prepared by reacting a compound of formula (I') wherein $R^1$ and $R^2$ are hydrogen, with an intermediate of formula (IV) or a functional derivative thereof.

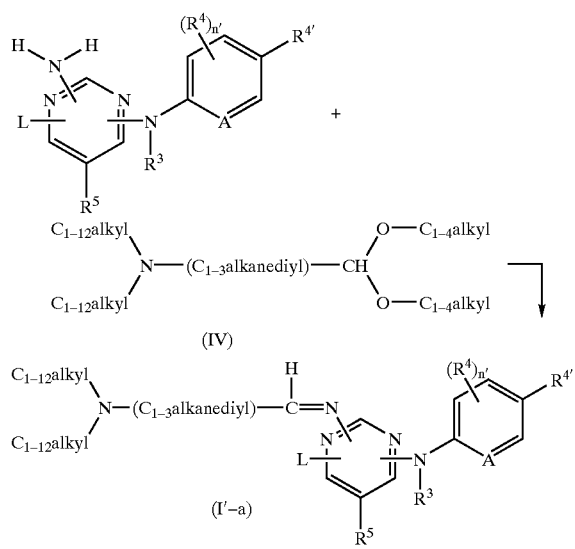

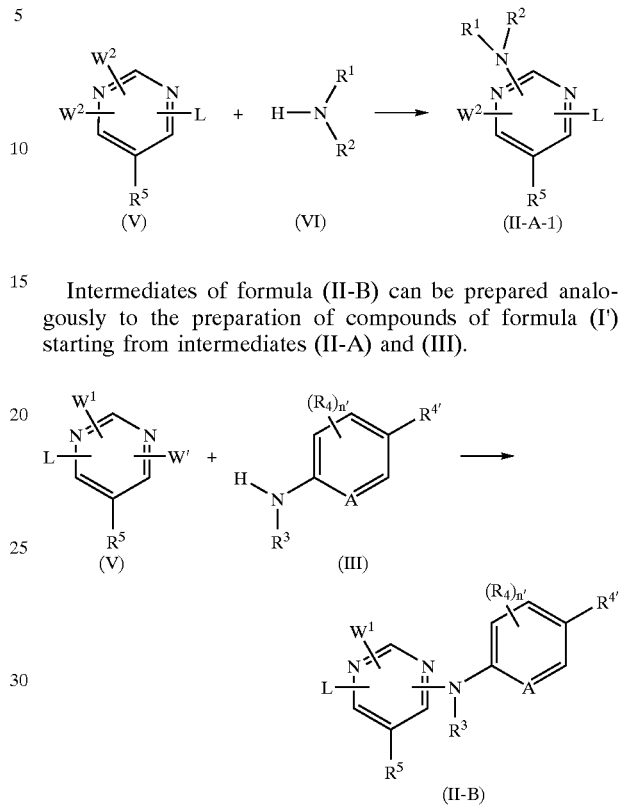

Also, compounds of formula (I') wherein Q is NR$^1$R$^2$ and R$^1$ and R$^2$ are hydrogen may further be reacted with an acyl halide or an alkyl chloroformate in a reaction-inert solvent such as, for example dichloromethane, in the presence of a suitable base, such as, for example, pyridine, to form the corresponding amide, respectively, carbamate derivative.

Some of the compounds of formula (I') and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distributions liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods, and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I') and intermediates involves liquid chromatography, in particular liquid chromatography using a chiral stationary phase.

The above specified reaction procedures for the preparation of compounds of formula (I') or subgroups thereof, can also be applied for the preparation of compounds of formula (I).

Some of the intermediates and starting materials are known compounds and may be commercially available or may be prepared according to art-known procedures.

Intermediates of formula (II-A) wherein Q is NR$^1$R$^2$, said intermediates being represented by formula (II-A-1), can be prepared by reacting a pyrimidine derivative of formula (V) wherein W$^2$ is a suitable leaving group such as, for example, a halogen, with HNR$^1$R$^2$ (VI) in a reaction inert solvent such as, for example, 1,4-dioxane, 2-propanol or the like. Different regio-specific isomers may be formed and can be separated from one another using suitable separation techniques such as, for example, chromatography.

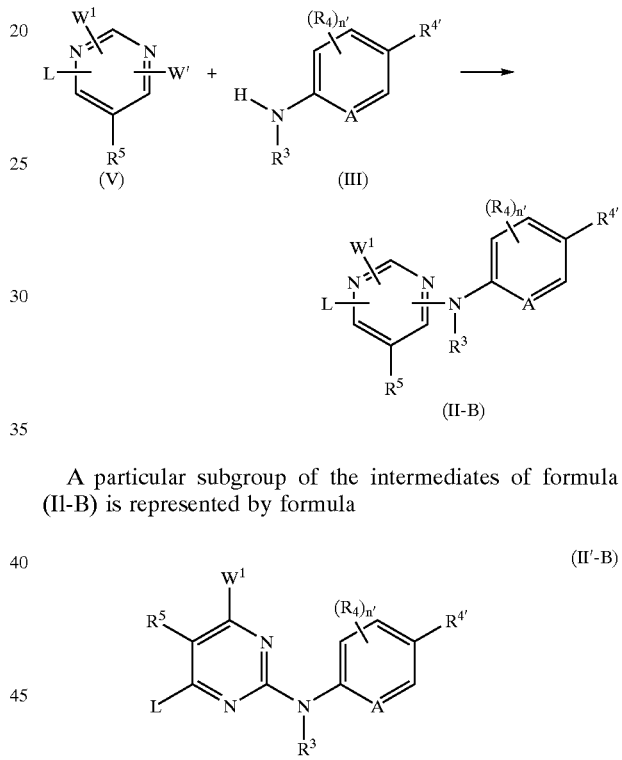

Intermediates of formula (II-B) can be prepared analogously to the preparation of compounds of formula (I') starting from intermediates (II-A) and (III).

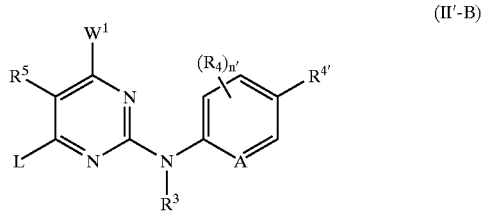

A particular subgroup of the intermediates of formula (II-B) is represented by formula (II'-B)

Particular intermediates of formula (II'-B) are those wherein W$^1$ is a halogen, more in particular, a chloro atom.

Intermediates of formula (V) whereby Q is NR$^1$R$^2$ and the L is L'—CH$_2$ and is attached in the 2 position of the pyrimidine ring and W$^2$ is chloro, said intermediates being represented by formula (V-a), can be prepared by reacting an imidamide of formula (VII) with a propanedioic acid ester of formula (VIII) in a solvent such as, for example, ethanol, and in the presence of, for instance, sodium, and subsequently reacting the thus formed intermediate of formula (IX) with a suitable reagent such as, for example, phosphoryl chloride.

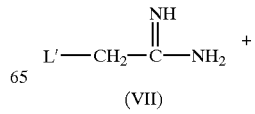

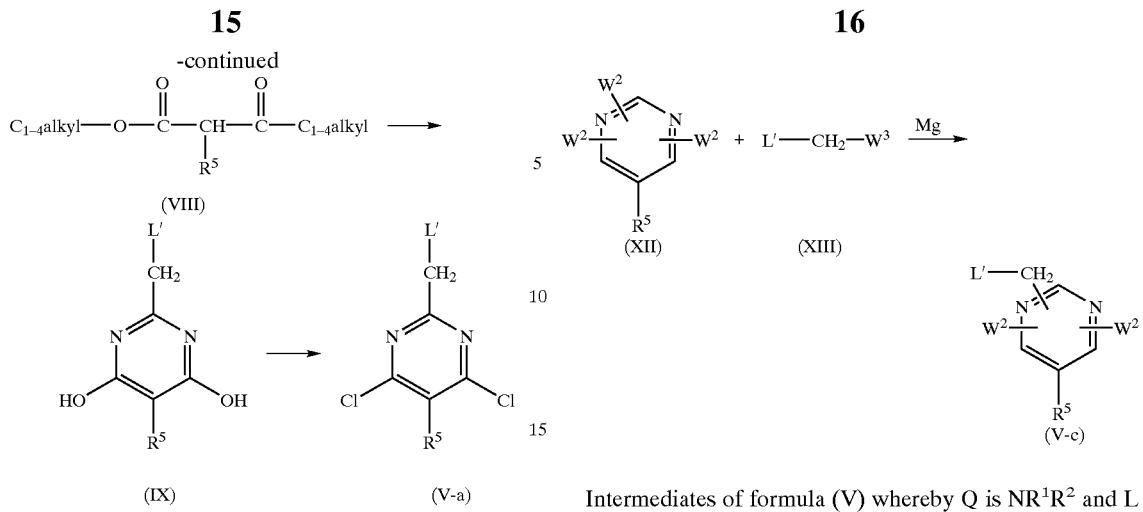

(VIII)

(IX) → (V-a)

Intermediates of formula (V) whereby Q is NR$^1$R$^2$ and L is L'—CH$_2$ and is attached in the 4 or 6 position of the pyrimidine ring and W$^2$ is chloro, said intermediates being represented by formula (V-b), can be prepared by reacting an intermediate of formula (X) with urea or a functional derivative thereof, in a solvent such as, for example, ethanol, and in the presence of, for instance, sodium, and subsequently reacting the thus formed intermediate of formula (XI) with a suitable reagent such as, for example, phosphoryl chloride.

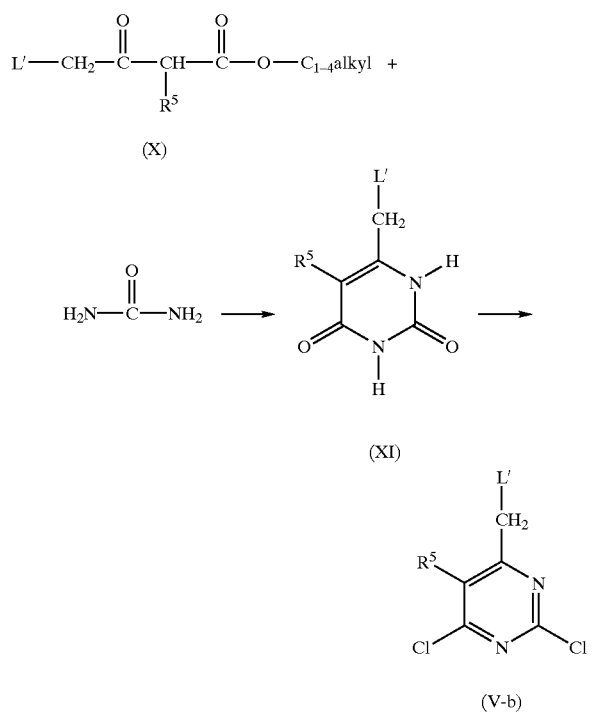

Intermediates of formula (V) wherein Q is NR$^1$R$^2$ and L is L'—CH$_2$ and is attached anywhere on the pyrimidine ring, said intermediates being represented by formula (V-c), can be prepared by reacting an intermediate of formula (XII-1), for Q is NR$^1$R$^2$ and formula (XII-2) for Q is hydrogen, wherein W$^2$ is a suitable leaving group such as, for example, a halogen, with an intermediate of formula (XIII) wherein W$^3$ is a suitable leaving group such as, for example, a halogen, according to the procedure of a Grignard reaction.

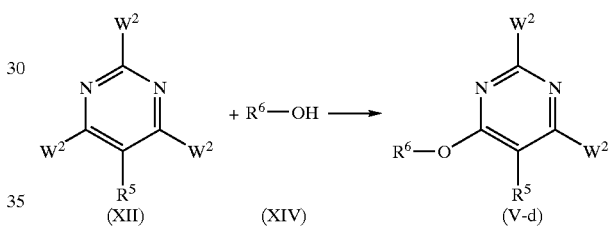

Intermediates of formula (V) whereby Q is NR$^1$R$^2$ and L is —O—R$^6$ or —NH—R$^6$ and is attached in the 4 or 6 position of the pyrimidine ring, said intermediates being represented by formula (V-d), can be prepared by reacting an intermediate of formula (XIV) with an intermediate of formula (XII) wherein W$^2$ is a suitable leaving group such as, for example, a halogen, in a reaction-inert solvent such as, for example, tetrahydrofuran or 1,4-dioxane, and in the presence of a suitable base such as, for example, potassium hydroxide or diisopropyl ethaneamine, or sodium hydride.

The intermediates of formula (V-a) to (V-d) can analogously be prepared for the compounds of formula (I') wherein Q is hydrogen. To this effect, there is one leaving group W$^2$ less on the pyrimidine ring of the respective starting material.

Compounds of formula (I') and some of the intermediates may have one or more stereogenic centers in their structure, present in a R or a S configuration.

The compounds of formula (I') as prepared in the hereinabove described processes may be synthesized as a mixture of stereoisomeric forms, in particular in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of the present invention and the intermediates of formula (II'-B) show antiretroviral properties, in particular against Human Immunodeficiency Virus (HIV), which is the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an everdecreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia. Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

The present compounds also show activity against HIV-1 strains that have acquired resistance to art-known non-nucleoside reverse transcriptase inhibitors. They also have little or no binding affinity to human α-1 acid glycoprotein.

Due to their antiretroviral properties, particularly their anti-HIV properties, especially their anti-HIV-1-activity, the compounds of the present invention are useful in the treatment of individuals infected by HIV and for the prophylaxis of these individuals. In general, the compounds of the present invention may be useful in the treatment of warm-blooded animals infected with viruses whose existence is mediated by, or depends upon, the enzyme reverse transcriptase. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic CNS diseases caused by retroviruses, such as, for example HIV mediated dementia and multiple sclerosis.

The compounds of the present invention or any subgroup thereof may therefore be used as medicines against above-mentioned conditions. Said use as a medicine or method of treatment comprises the systemic administration to HIV-infected subjects of an amount effective to combat the conditions associated with HIV and other pathogenic retroviruses, especially HIV-1.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

It is especially advantageous to formulate the aforementioned pharmaceutical compositions in dosage unit form for ease of administration and uniformity of dosage. Dosage unit form as used herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions and the like, and segregated multiples thereof.

Those of skill in the treatment of HIV-infection could determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the seventy of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

Also, the combination of an antiretroviral compound and a compound of the present invention can be used as a medicine. Thus, the present invention also relates to a product containing (a) a compound of the present invention, and (b) another antiretroviral compound, as a combined preparation for simultaneous, separate or sequential use in anti-HIV treatment. The different drugs may be combined in a single preparation together with pharmaceutically acceptable carriers. Said other antiretroviral compounds may be known antiretroviral compounds such as nucleoside reverse transcriptase inhibitors, e.g. zidovudine (3'-azido-3'-deoxythymidine, AZT), didanosine (dideoxy inosine; ddI), zalcitabine (dideoxycytidine, ddC) or lamivudine (3'-thia-2'-3'-dideoxycytidine, 3TC) and the like; non-nucleoside reverse transcriptase inhibitors such as suramine, foscarnet-sodium (trisodium phosphonoformate), nevirapine (11-cyclopropyl-5,11-dihydro-4-methyl-6H-dipyrido[3,2-b: 2',3'-e] [1,4]diazepin-6-one), sustiva (efavirenz), tacrine (tetrahydroaminoacridine) and the like; compounds of the TIBO (tetrahydro-imidazo[4,5,1-jk][1,4]-benzodiazepine-2 (1H)-one and thione)-type e.g. (S)-8-chloro-4,5,6,7-tetrahydro-5-methyl-6-(3-methyl-2-butenyl)imidazo-[4,5,1-jk][1,4]benzodiazepine-2(1H)-thione; compounds of the α-APA (α-anilino phenyl acetamide) type e.g. α-[(2-nitro-phenyl)amino]-2,6-dichloro-benzene-acetamide and the like: TAT-inhibitors, e.g. RO-5-3335 and the like; protease inhibitors e.g. indinavir, ntanovir, saquinovir and the like; NMDA receptor inhibitors e.g. pentamidine; α-glycosidase inhibitor e.g. castanospermine and the like; Rnase H inhibitor e.g. dextran (dextran sulfate) and the like; or immunomodulating agents, e.g. levamisole, thymopentin and the like.

The following examples are intended to illustrate the present invention.

EXPERIMENTAL PART

A. Intermediate Compounds

Example A1 a) A solution of 2,6-dichlorobenzylchloride (0.102 mol) in 1,1-diethylether (10 ml) was added dropwise to magnesium (0.102 mol) in 1,1-diethylether (60 ml). The reaction was initiated by adding 2 drops of 1,2-dibromoethane. After most of magnesium disappeared, 2,4,6-trichloropyrimidine (0.051 mol) in 1,1-diethylether (30 ml) was added. The mixture was stirred overnight at room temperature. The solvent was evaporated and the residue was purified by flash column chromatography over silica gel (eluent: $CH_2Cl_2$/hexane ½). The desired fractions were collected and the solvent was evaporated, yielding 3.3 g of (21%) 2,4-dichloro-6-[(2,6-dichloro-phenyl)methyl]pyrimidine (interm. 1; m.p.: 106–107° C.).

b) Intermediate (1) (0.0081 mol) in 2-propanol (100 ml) was heated until complete dissolution. The solution was then transferred into a pressure tube and $NH_3$ gas was bubbled into it for 20 minutes. Then the mixture was heated to 80° C. for 16 hours. The solvent was evaporated, yielding a residue of two compounds: 2-chloro-6-[(2,6-di-chloro-phenyl)methyl]-4-pyrimidinamine (interm. 2) and 4-chloro-6-[(2,6-dichloro-phenyl)methyl]-2-pyrimidinamine (interm. 3).

Example A2 a) Urea (0.03 mol) was added to a mixture of (±)-ethyl 2,6-dichloro-phenyl-α-methyl-β-oxobutanoate (0.02 mol) in $NaOC_2H_5$ in ethanol, (1M; 0.040 mol; 40 ml). The reaction mixture was stirred and refluxed overnight. The solvent was evaporated, water was added and the mixture was neutralized with 0.3 N HOAc. The precipitate was filtered off and was further triturated with ether and then $H_2O$, then filtered off and dried, yielding 2.2 g (39%) of 6-[(2,6-dichloro-phenyl)methyl]-5-methyl-2,4(1H,3H)-pyrimidinedione (interm. 4).

b) A mixture of intermediate (4) (0.0095 mol) in phosphoryl chloride (50 ml) was stirred and refluxed overnight. Excess of phosphoryl chloride was then evaporated. Ice-water was added to the residue. A white precipitate was formed, filtered off and dried. The residue was purified by flash column chromatography over silica gel (eluent: $CH_2Cl_2$). The desired fractions were collected and the solvent was evaporated, yielding 2.06 g (67%) of 2,4-dichloro-6-[(2,6-dichloro-phenyl)methyl]-5-methyl-pyrimidine (interm. 5).

c) 4-chloro-6-[(2,6-dichloro-phenyl)methyl]-5-methyl-2-pyrimidinamine (interm. 6) and 2-chloro-6-[(2,6-dichloro-phenyl)methyl]-5-methyl-4-pyrimidinamine (interm. 7) were prepared from intermediate 5 following the procedures as described in example A1b.

Example A3 a) To the stirred solution of 2,6-dichlorobenzeneethanimidamide HCl (1:1), (0.0042 mol) in ethanol (20 ml), a solution of sodium (0.013 mol) in ethanol (10 ml) was added dropwise first and then propanedioic acid, diethyl ester (0.0109 mol) was added. The reaction mixture was stirred and refluxed for 4 hours and then stirred at room temperature overnight. After adding another equivalent of propanedioic acid, diethyl ester (stirring and refluxing it overnight), the solvent was evaporated and the residue was dissolved in water and acidified with 1 N HCl. The solid was filtered off, washed with water and dried, yielding 0.87 g (76.4%) of 2-[(2,6-dichloro-phenyl)methyl]-4,6-pyrimidinediol (interm. 8).

b) 6-chloro-2-[(2,6-dichloro-phenyl)methyl]-4-pyrimidinamine (interm. 9) was prepared starting from intermediate 8 according to the procedures described in example A.1.b, A2.b & A2.c.

Example A4

4-Amino-1-butanol (1.57 ml) was added to a solution of intermediate (1) (0.008 mol) in 1,4-dioxane (20 ml) under Argon. The reaction mixture was stirred for 2 hours at room temperature. The solvent was evaporated. The residue was purified by flash column chromatography over silica gel (eluent gradient: $CH_2Cl_2$/$CH_3OH$: from 100/0 to 98/2). The pure fractions were collected and the solvent was evaporated, yielding 2.05 g of a mixture of 4-[[2-chloro-6-[(2,6-dichloro-phenyl)methyl]-4-pyrimidinyl]-amino]-1-butanol (interm. 10) and 4-[[4-chloro-6-[(2,6-dichloro-phenyl)methyl]-2-pyrimidinyl]amino]-1-butanol (interm. 11).

Example A5 a) Potassium hydroxide/ethanol (10%; 0.035 mol) was added to a solution of 2,6-dichlorophenol (0.035 mol) in tetrahydrofuran (100 ml). The mixture was stirred and 2,4,6-trichloropyrimidine (0.044 mol) was added. The mixture was stirred overnight at 60° C. The reaction was quenched with NaOH 1N solution. The aqueous layers were extracted with EtOAc several times and then the organic layers were combined and washed with NaOH 3N and saturated NaCl, dried and concentrated. The residue was recrystallized from $CH_2Cl_2$/hexane. The precipitate was filtered off and dried, yielding 5.98 g 2,4-dichloro-6-(2,6-dichlorophenoxy)pyrimidine (55%) (interm. 12).

b) Reaction under Argon atmosphere, 2,4,6-trimethylaniline (0.0678 mol) was added to 2,4-dichloropyrimidine (0.0664 mol) in 1,4-dioxane (100 ml). N,N-di(1-methylethyl)-ethaneamine (0.0830 mol) was added. The reaction mixture was stirred and refluxed for 4 days and the solvent was evaporated. The residue was dissolved in $CH_2Cl_2$, washed with a saturated $NaHCO_3$ solution, then dried ($Na_2SO_4$), filtered and the solvent was evaporated to give 17.1 g solid residue. This solid was dissolved in CH$_2$Cl$_2$:hexane (1:1; 150 ml), and the resulting solution was concentrated to 100 ml, then filtered. The residue was purified by column chromatography on KP-Sil (eluent: CH$_2$Cl$_2$). The desired fractions were collected and the solvent was evaporated. The less polar fraction was stirred in CH$_2$Cl$_2$ for 3 hours and filtered, yielding 0.44 g 4-chloro-N-(2,4,6-trimethylphenyl)-2-pyrimidinamine (intermediate 48). A second fraction was recrystallized from acetonitrile, filtered off and dried, yielding 2-chloro-N-(2,4,6-trimethyl-phenyl)-4-pyrimidinamine (intermediate 49).

Example A6

Pyridine (1 ml) was added to a mixture of 4-[[4-amino-6-[(2,6-dichloro-phenyl)-methyl]-2-pyrimidinyl]amino]benzonitrile (0.00135 mol) in CH$_2$Cl$_2$ (19 ml). A solution of chloroethanoyl chloride (0.001375 mol) in CH$_2$Cl$_2$ (0.5 ml) was added dropwise on an ice bath. The mixture was stirred at room temperature for 2 hours. More chloroethanoyl chloride (0.00625 mol) in CH$_2$Cl$_2$ (0.5 ml) was added. The mixture stood in the refrigerator overnight. The solvent was evaporated. The residue was treated with a saturated Na$_2$CO$_3$ solution and the mixture was extracted with CH$_2$Cl$_2$. The separated organic layer was dried, filtered and concentrated. The residue was purified by flash column chromatography over silica gel (eluent: CH$_2$Cl$_2$/CH$_3$OH/NH$_4$OH 99/1/0.1). The desired fractions were collected and the solvent was evaporated, yielding 0.22 g (36.5%) of 2-chloro-N-[6-[(2,6-dichloro-phenyl)methyl]-2-[(4-cyanophenyl)amino]-4-pyrimidinyl]acetamide (interm. 13).

Example A7

A mixture of 4-[(4-chloro-2-pyrimidinyl)amino]benzonitrile (0.005 mol) and nitryl tetrafluoroborate (0.0025 mol) in acetonitrile (5 ml) was stirred at room temperature for 4 h. The material was quenched with saturated bicarbonate (50 ml) on cracked ice. The mixture was allowed to reach room temperature, and the yellow solid was filtered off. The solid was adsorbed onto silica and purified by column chromatography (eluent: 30%, 50%, 60%, 70% CH$_2$Cl$_2$ in hexanes). The solvent of the desired fraction was evaporated and the residue was dried, yielding 0.89 g (64%) of 3-nitro-4-[(4-chloro-2-pyrimidinyl)amino]benzonitrile. (interm. 51)

Example A8

A mixture of 2,6-dichloro-N-(2,4,6-trimethylphenyl)-4-pyrimidinamine (0.00376 mol) in a 2.0 M solution of NH$_3$ in 2-propanol (25 ml) and a 0.5 M solution of NH$_3$ in dioxane (25 ml) was heated in a pressure sample at 110–115° C. for 24 hours. The solvent was evaporated, and the residue was chromatographed on Biotage (eluent: 1:1 CH$_2$Cl$_2$:hexane). The desired fractions were collected and the solvent was evaporated, yielding a mixture of 0.523 g of 2-chloro-N4-(2,4,6-trimethylphenyl)-4,6-pyrimidinediamine (interm. 53) and 0.101 g of 6-chloro-N4-(2,4,6-trimethylphenyl)-2,4-pyrimidinediamine, (interm. 50)

Tables 1 and 2 list intermediates which were prepared analogous to one of the above examples.

TABLE 1a

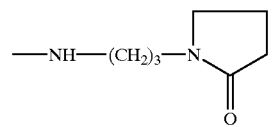

| Int. No. | Ex. No. | $R^a$ | $R^b$ | $R^c$ | X | $R^5$ | R | physical data melting point |
|---|---|---|---|---|---|---|---|---|
| 6 | A2c | Cl | H | Cl | CH$_2$ | CH$_3$ | —NH$_2$ | — |
| 15 | A1b | Cl | H | Cl | CH$_2$ | H | —NH—CH$_3$ | — |
| 16 | A1b | Cl | H | Cl | O | H | —NH—CH$_3$ | 152–155° C. |
| 17 | A1b | Cl | H | Cl | O | H | —NH$_2$ | — |
| 19 | A4 | Cl | H | Cl | CH$_2$ | H | —NH—(CH$_2$)$_3$—OH | — |
| 20 | A4 | Cl | H | Cl | CH$_2$ | H | —NH—(CH$_2$)$_2$—OH | 111–113° C. |
| 21 | A4 | Cl | H | Cl | CH$_2$ | H | —NH—CH$_2$—CH(OH)—C$_6$H$_5$ | 133–134° C. |
| 22 | A4 | Cl | H | Cl | CH$_2$ | H | —NH—(CH$_2$)$_3$—N(pyrrolidinone) | — |
| 23 | A4 | Cl | H | Cl | CH$_2$ | H | —NH—(CH$_2$)$_2$—O—(CH$_2$)$_2$OH | 99–107° C. |
| 24 | A4 | Cl | H | Cl | CH$_2$ | H | —NH—(CH$_2$)$_2$—(4-OCH$_3$—C$_6$H$_4$) | 138–140° C. |
| 25 | A4 | Cl | H | Cl | CH$_2$ | H | —NH—(CH$_2$)$_2$—(3-OCH$_3$—C$_6$H$_4$) | 132–135° C. |
| 26 | A4 | Cl | H | Cl | CH$_2$ | H | —NH—CH$_2$—CH(OH)—CH$_2$OH | 116–118° C. |
| 27 | A4 | Cl | H | Cl | CH$_2$ | H | —NH—CH$_2$—C$_6$H$_5$ | 137–139° C. |
| 28 | A4 | Cl | H | Cl | CH$_2$ | H | —NH—(CH$_2$)$_2$-(2-thienyl) | 113–114° C. |
| 29 | A4 | Cl | H | Cl | CH$_2$ | H | —NH—(CH$_2$)$_2$-(2-pyridyl) | 113.5–114° C. |
| 31 | A4 | Cl | H | Cl | CH$_2$ | H | —NH—(CH$_2$)$_2$CN | 151–153° C. |
| 48 | A5b | CH$_3$ | CH$_3$ | CH$_3$ | NH | H | —H | 142–143° C. |
| 50 | A8 | CH$_3$ | CH$_3$ | CH$_3$ | NH | H | —NH$_2$ | |

TABLE 1b

[Structure: pyrimidine with R⁵, Cl at 4,5-positions; R at 6; connected at 2-position via X to phenyl bearing R⁴, Rᵇ, Rᶜ]

| Int. No. | Ex. No. | Rᵃ | Rᵇ | Rᶜ | X | R⁵ | R | physical data melting point |
|---|---|---|---|---|---|---|---|---|
| 14 | A2b | H | CN | H | NH | H | H | 211–212° C. |
| 18 | A5b | CH₃ | CH₃ | CH₃ | NH | CH₃ | H | |
| 30 | A2b | H | CN | H | NH | CH₃ | H | |
| 51 | A7 | NO₂ | CN | H | NH | H | H | 142–144° C. |

TABLE 2

[Structure: phenyl bearing Rᵃ, Rᵇ, Rᶜ connected via X to pyrimidine with R⁵, R at 5,6-positions and Cl at 2-position]

| Int. No. | Ex. No. | Rᵃ | Rᵇ | Rᶜ | X | R⁵ | R | physical data |
|---|---|---|---|---|---|---|---|---|
| 7 | A2c | Cl | H | Cl | CH₂ | CH₃ | —NH₂ | |
| 32 | A1b | Cl | H | Cl | CH₂ | H | —NH—CH₃ | — |
| 33 | A4 | Cl | H | Cl | CH₂ | H | —NH—(CH₂)₂-(1-pyrrolidinyl) | 134–135° C. |
| 34 | A4 | Cl | H | Cl | CH₂ | H | —NH—(CH₂)₂-(2-pyridyl) | 130–133° C. |
| 35 | A4 | Cl | H | Cl | CH₂ | H | —NH—(CH₂)₂-(2-thienyl) | 98–99° C. |
| 36 | A4 | Cl | H | Cl | CH₂ | H | —NH—(CH₂)₂-(3-OCH₃—C₆H₄) | 104–109° C. |
| 37 | A4 | Cl | H | Cl | CH₂ | H | —NH—(CH₂)₂-(4-OCH₃—C₆H₄) | 149–150° C. |
| 38 | A4 | Cl | H | Cl | CH₂ | H | —NH—(CH₂)₂CN | 137–139° C. |
| 39 | A4 | Cl | H | Cl | CH₂ | H | —NH—(CH₂)₂—O—(CH₂)₂OH | |
| 40 | A4 | Cl | H | Cl | CH₂ | H | —NH—(CH₂)₂OH | 170–173° C. |
| 41 | A4 | Cl | H | Cl | CH₂ | H | —NH—(CH₂)₃—O—CH(CH₃)₂ | — |
| 42 | A4 | Cl | H | Cl | CH₂ | H | —NH—(CH₂)₃—OH | — |
| 43 | A4 | Cl | H | Cl | CH₂ | H | —NH—CH₂—C₆H₅ | 171–172° C. |
| 45 | A4 | Cl | H | Cl | CH₂ | H | —NH—CH₂—CH(OH)—CH₂OH | >60° C. |
| 46 | A4 | Cl | H | Cl | CH₂ | H | —NH—O—CH₂—C₆H₅ | 137–141° C. |
| 47 | A4 | Cl | H | Cl | CH₂ | H | —NH—(CH₂)₃—N(pyrrolidin-2-one) | 55–60° C. |
| 49 | A5b | CH₃ | CH₃ | CH₃ | NH | H | H | 182–183° C. |
| 52 | A4 | Cl | H | Cl | CH₂ | H | —NH—CH₂—CH(OH)—C₆H₅ | 75–83° C. |
| 53 | A1b | CH₃ | CH₃ | CH₃ | NH | H | —NH₂ | |
| 54 | A5b | CH₃ | CH₃ | CH₃ | NH | CH₃ | H | |
| 55 | A5a | Cl | Cl | Cl | —O— | H | H | 159–161° C. |

B. Compounds of Formula (I')

Example B1

A mixture of intermediate (42) and intermediate (19) (0.004 mol) and 4-amino-benzonitrile (0.0084 mol) were combined in a sealed tube and heated for 16 hours at 160° C. under Argon. The reaction mixture was allowed to cool to room temperature and dissolved in $CH_2Cl_2/CH_3OH$ 90/10 (20 ml) and 5 g of silica gel was added. After evaporating the solvent, the residue was purified by flash column chromatography over silica gel (eluent oradient: $CH_2Cl_2/CH_3OH$: from 100/0 to 97/3). The desired fraction was collected and the solvent was evaporated, yielding 0.31 g (18.1%) of 4-[[4-[(2,6-dichloro-phenyl)methyl]-6-((3-hydroxypropyl)amino]-2-pyrimidinyl]amino benzonitrile (compound 3).

Example B2

Intermediates (47) and (22) (0.00399 mol) and 4-aminobenzonitrile (0.0012 mol) in 1-methyl-2-pyrrolidinone (3 ml) was stirred for 16 hours at 130° C. under Argon. Then, the reaction mixture was cooled to room temperature and quenched with $H_2O$ (200 ml). A precipitate formed, which was stirred for 16 hours, and separated by filtration over Celite. The residue was dissolved in $CH_3OH/CH_2Cl_2$ (10%, 200 ml), dried over $K_2CO_3$, filtered, and evaporated. This resulting material was further purified by flash column chromatography over silica gel (gradient eluent: $CH_2Cl_2/CH_3OH$ from 100/0 to 95/5). The desired fraction was collected and the solvent was evaporated, yielding 0.43 g (21.7%) of 4-[[6-[(2,6-dichloro-phenyl)methyl]-2-[[3-(2-oxo-1-pyrrolidinyl)propyl]-amino]-4-pyrimidinyl]amino]benzonitrile (comp. 39: 104–114° C.).

Example B3

HCl/diethyl ether (1N; 2.77 ml) was stirred into a solution of intermediate (33) (0.00277 mol) in 1-methyl-2-pyrrolidinone (4 ml) under $N_2$ atmosphere. The reaction mixture was heated for 5 minutes. Next, 4-aminobenzonitrile (0.0061 mol) was added and the reaction was heated at 100° C. for 16 hours. Then, the reaction mixture was cooled to room temperature and diluted with ethylacetate (10 ml). The organic layer was washed with NaOH (1 N; 2×100 ml), $H_2O$ (2×100 ml), brine (50 ml), respectively, dried, filtered and the filtrate was evaporated. The crude material was purified by flash chromatography (eluent: 2.5–7.5% of $CH_3OH$ containing 10% $NH_4OH$ in $CH_2Cl_2$). The desired fractions were collected and the solvent was evaporated. The residue was dried, yielding 0.160 g (12.0%) of 4-[[4-[(2,6-dichloro-phenyl)methyl]-6-[[2-(1-pyrrolidinyl)ethyl]amino]-2-pyrimidinyl]amino]benzonitrile (comp. 13: mp. 80–85° C.).

Example B4

A slurry of intermediate (14) (0.005 mol) in $CH_2Cl_2$ (150 ml) was stirred rapidly and cooled to 0° C. under nitrogen. $BBr_3$ (0.015 mol) was introduced by syringe. The reaction mixture was stirred rapidly for two hours. The reaction mixture was recooled to 0° C. and quenched with NaOH (aq. 1 N, 25 ml). The biphasic partial quench mixture gives a precipitate which was filtered off and dried, yielding 2.5 g (91%) of 4-[[4-[(2,6-dichloro-phenyl)methyl]-6-(hydroxyamino)-2-pyrimidinyl]amino]-benzonitrile dihydrobromide.pentahydrate (comp. 15; mp. 240–244° C.).

Example B5

1,1-Dimethoxy-N,N-dimethylmethanamine (0.152 mol) was added to 4-[[4-amino-6-[(2,6-dichlorophenyl)methyl]-2-pyrimidinyl]amino]benzonitrile (0.0008 mol). The mixture was stirred at room temperature for 2 days and then concentrated. The crude product was purified by trash chromatography over silica gel (eluent: $CH_2Cl_2/CH_3OH$ 99/1). The desired fraction was collected and the solvent was evaporated. The resulting residue was triturated with hexane, yielding 0.15 g (42%) of N'-[2-[(4-cyano-phenyl)amino]-6-[(2,6-dichlorophenyl)methyl]-4-pyrimidinyl]-N,N-dimethyl-methanimidamide (comp. 26; mp. 175–180° C.).

Example B6

Piperidine (0.12 ml) was added to a mixture of intermediate (13) (0.00047 mol) in tetrahydrofuran (20 ml). The mixture was stirred at room temperature for 4 hours. More piperidine (0.14 ml) was added. The mixture was stirred for another 2 hours. The solvent was evaporated. The residue was purified by flash column chromatography over silica gel ($CH_2Cl_2/CH_3OH/NH_4OH$ 99/1/0.1). The desired fractions were collected and the solvent was evaporated, yielding 0.05 g (21.5%) of N-[6-[(2,6-dichloro-phenyl)methyl]-2-[(4-cyano-phenyl)amino]-4-pyrimidinyl]-1-piperidine-acetamide (comp. 25: mp. 175–180° C.).

Example B7

Pyridine (0.014 mol) was added to a mixture of 4-[[4-amino-6-[(2,6-dichlorophenyl)-methyl]-2-pyrimidinyl]amino]benzonitrile (0.0013 mol) in $CH_2Cl_2$. A solution of octanoyl chloride (1.5 equiv) in $CH_2Cl_2$ (0.5 ml) was added dropwise. The mixture was stirred at room temperature for 2 hours. More octanoyl chloride (3,5 equiv) in $CH_2Cl_2$ was added dropwise. The mixture was stirred. The solvent was then evaporated. The residue was treated with a saturated aqueous $NaHCO_3$ solution and the mixture was extracted with $CH_2Cl_2$. The separated organic layer was dried, filtered and the solvent was evaporated to give the crude product. The residue was recrystallized from $CHCl_3$ and hexane, yielding 0.443 g (68.6%) of N-[6-[(2,6-dichloro-phenyl)methyl]-2-[(4-cyano-phenyl)amino]-4-pyrimidinyl]octanamide (comp. 17; mp. 135–137° C.).

Example B8 a) A mixture of intermediate 49 (0.082 mol) and 5.4 N HCl in 2-propanol (0.086 mol) in water (300 ml) was stirred and warmed to 40–45° C. over 30 minutes, 4-Aminobenzonitrile (0.242 mol) was added at 40–45° C. The reaction mixture was stirred and refluxed for 4.5 hours, then cooled to room temperature. This mixture was alkalized by portionwise addition of $NaHCO_3$. This mixture was extracted with ethylacetate. The organic layer was separated, washed with brine, dried, filtered and the solvent was evaporated. This fraction was stirred in ethanol p.a. (100 ml), filtered off, washed with ethanol (50 ml), then dried, yielding 23.1 g (86%) 4-[[4-[(2,4,6-trimethylphenyl)-amino]-2-pyrimidinyl]amino]benzonitrile (compound 52).

b) A mixture of 4-[(4-chloro-2-pyrimidinyl)amino]benzonitrile (0.021 mol) and HCl in 2-propanol (0.0095 mol) in water (30 ml) was stirred for one hour at 45° C. 4-amino-3,5-dimethyl-benzonitrile (0.025 mol) was added and the reaction mixture was stirred and refluxed overnight. The mixture was cooled to room temperature, then neutralized with $NaHCO_3$. This mixture was extracted with ethylacetate. The separated organic layer was washed with brine, dried, filtered and the solvent evaporated. The residue was crystallized from $CH_3CN$, filtered off and dried. The residue was stirred in boiling $CH_2Cl_2$ (20 ml), then filtered off and dried. The residue was crystallized from methyl isobutyl keton, filtered off and dried, yielding 0.3 g of 4-[[2-[(cyanophenyl)amino]-4-pyrimidinyl]amino]-3,5-dimethylbenzonitrile (compound 69).

Example B9 a) 4-[(4-chloro-2-pyrimidinyl)amino]benzonitrile (0.003 mol), 2,6-dibromo-4-methyl-benzenamine (0.006 mol) and 1 M HCl in diethyl ether (4.5 ml) in 1,4-dioxane (10 ml) were combined in a tube and heated under Ar until all diethyl ether had evaporated. The tube was sealed and heated at 170° C. for 2.5 days. Silica gel was added, and the solvent was evaporated. The residue was purified by flash column chromatography over silica gel (eluent gradient: $CH_2Cl_2:CH_3OH:NH_4OH$ 100:0:0 to 99:0.9:0.1). The desired fractions were collected and the solvent was evaporated. The residue was recrystallized from acetonitrile, filtered off and dried, yielding 0.22 g (15.9%) of 4-[[4-[(2,6-dibromo-4-methylphenyl)amino]-2-pyrimidinyl]amino]benzonitrile (compound 61).

b) 4-[[4-[(4-chloro-5-methyl-2-pyrimidinyl]amino]benzonitrile (0.01541 mol), 4-amino-3,5-dimethyl-benzonitrile (0.00219 mol), 1-methyl-2-pyrrolidinone (4 ml), 1,4-dioxane (15 ml) and diisopropylethylamine (0.0154 mol) were combined in a flask under a stream of argon and heated at 160–230° C. for 16 hours. $CH_2Cl_2$ and 1N NaOH were added, and the mixture was stirred 1 hour and filtered to give a brown solid (*). The $CH_2Cl_2$ filtrate was separated and was evaporated and purified by flash column chromatography (eluent: 2% $CH_3OH/CH_2Cl_2$). The desired fractions were combined, evaporated and the residue was stirred in $CH_2Cl_2$. The solid precipitate was filtered off, combined with the brown solid (*) and recrystallized from $CH_3CN$. The precipitate was filtered off and dried, yielding 1.57 g (29%) of 4-[[2-[(4-cyanophenyl)amino]-5-methyl-4-pyrimidinyl]amino]-3,5-dimethylbenzonitrile (compound 89).

c) 2-[(4-cyanophenyl)amino]-4-pyrimidinyl trifluoromethanesulfonate (0.0022 mol) and 2,6-dichloro-4-(trifluoromethyl)-benzenamine (0.0044 mol) were combined in 1,4-dioxane (2.5 ml) and heated in a sealed tube under Ar at 170° C. for 40 hours. The reaction mixture was allowed to cool to room temperature. Silica gel was added, and the solvent was evaporated. The residue was purified by flash column chromatography over silica gel (eluent gradient: $CH_2Cl_2:CH_3OH:NH_4OH$ 100:0:0 to 97:2.7:0.3). The desired fractions were collected and the solvent was evaporated. The residue was recrystallized from $CH_3CN$, filtered off and dried, yielding 0.086 g (9.2%) of 4-[[4-[[2,6-dichloro-4-(trifluoromethyl)-phenyl]amino]-2-pyrimidinyl]amino]benzonitrile (compound 66).

Example B10

To a suspension of NaH (0.006 mol) in 1,4-dioxane (30 ml), 2,4,6-trimethyl-phenol (0.006 mol) was added. The mixture was stirred for 15 minutes at room temperature, and a clear solution formed, 4-[(4-chloro-2-pyrimidinyl)amino]benzonitrile (0.004 mol) was added, and the reaction mixture was heated to reflux under Argon for 15 hours. The reaction mixture was allowed to cool to room temperature, 0.5 ml of water was added, followed by 4 g of silica gel, and the solvent was evaporated. The residue was purified by flash column chromatography over silica gel (eluent gradient: $CH_2Cl_2:CH_3OH$ 100:0:0 to 97:3). The pure fractions were collected and the solvent was evaporated, yielding 1.18 g (89.4%) of 4-[[4-(2,4,6-trimethylphenoxy)-2-pyrimidinyl]amino]benzonitrile (compound 58).

Example B11

Compound (52) (0.0015 mol) was stirred in boiling ethanol (8 ml), 6 M HCl in 2-propanol (0.0015 mol) was added and the salt was allowed to crystallize out overnight at room temperature. The precipitate was filtered off, washed with 2-propanol and dried, yielding 0.47 g (86%) of 4-[[4-[(2,4,6-trimethyl-phenyl)amino]-2-pyrimidinyl]amino]benzonitrile hydrochloride (1:1) (compound 53).

Example B12

A mixture of compound (52) (0.00303 mol) and $NaBO_3.4H_2O$ (0.00911 mol) in $CH_3OH$ (30 ml) and $H_2O$ (10 ml) was stirred and refluxed for 4 days. The reaction mixture was cooled. The precipitate was filtered off and the precipitate (*) was purified by flash column chromatography over silica gel (eluent: $CH_2Cl_2/CH_3OH$ gradient from 100/0 to 95/5). The desired fractions were collected and the solvent was evaporated, yielding 0.586 g (56%) of 4-[[4-[(2,4,6-trimethylphenyl)amino]-2-pyrimidinyl]amino]benzamide (compound 100). The filtrate (*) was purified by reversed-phase HPLC (eluent gradient: ((0.5% aminoniumacetate in $H_2O$)/$CH_3CN$ 90/10)/$CH_3OH/CH_3CN$ (0 minutes) 75/25/0, (44 minutes) 0/50/50, (57 minutes) 0/0/100, (61.1–70 minutes) 75/25/0). Three desired fraction groups were collected and their solvent was evaporated, yielding 0.18 g of 4-[[4-[(2,4,6-trimethylphenyl)amino]-2-pyrimidinyl]amino]benzamide, N3-oxide (compound 106) and 0.030 g of 4-[[4-[(2,4,6-trimethylphenyl)amino]-2-pyrimidinyl]amino]benzamide, N1-oxide (compound 107).

Tables 3, 4, 5 and 6 list the compounds of formula (I) that were prepared according to one of the above examples.

TABLE 3

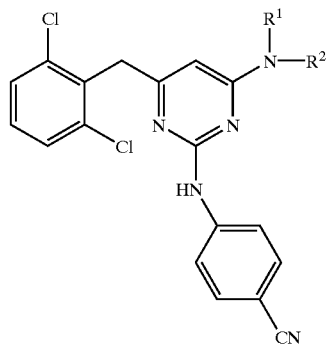

| Co. No. | Ex. No. | $NR^1R^2$ | physical data (melting point in ° C.) |
|---|---|---|---|
| 1 | B2 | —NH—$(CH_2)_4$—OH | 161–163° C. |
| 2 | B2 | —NH—$(CH_2)_2$—OH | 207–210° C. |

TABLE 3-continued

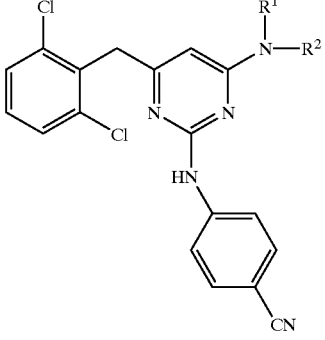

| Co. No. | Ex. No. | NR¹R² | physical data (melting point in ° C.) |
|---|---|---|---|
| 3 | B2 | —NH—(CH₂)₃—OH | 152–154° C. |
| 4 | B2 | —NH—CH₂—CHOH—C₆H₅ | 158–165° C. |
| 5 | B2 | —NH—(CH₂)₃—N(1-pyrrolidin-2-one) | 48–56° C. |
| 6 | B2 | —NH—(CH₂)₂—O—(CH₂)₂—OH | 162–175° C.; HCl (1:1) |
| 7 | B2 | —NH—(CH₂)₃—O—CH(CH₃)₂ | 181–182° C.; HCl (1:1) |
| 8 | B2 | —NH—(CH₂)₂-(3-OCH₃—C₆H₄) | 72–80° C. |
| 9 | B2 | —NH—CH₂—CHOH—CH₂OH | 189–192° C. |
| 10 | B2 | —NH—(CH₂)₂-(4-OCH₃—C₆H₄) | 72–80° C. |
| 11 | B2 | —NH—O—CH₂—C₆H₅ | — |
| 12 | B2 | —NH—CH₂—C₆H₅ | — |
| 13 | B3 | —NH—(CH₂)₂-(1-pyrrolidinyl) | 80–85° C. |
| 14 | B2 | —NH—(CH₂)₂-(2-thienyl) | — |
| 15 | B4 | —NH—OH | 240–244° C. |
| 16 | B2 | —NH—(CH₂)₂—(2-pyridyl) | 75–80° C. |
| 17 | B7 | —NH—CO—C₇H₁₅ | 135–137° C. |
| 18 | B7 | —NH—CO—C₁₁H₂₃ | 130–135° C. |
| 19 | B2 | —NH—(CH₂)₂—CN | 255° C. HCl (1:1) |
| 20 | B7 | —NH—CO—O—C₂H₅ | >200° C. |
| 21 | B7 | —NH—CO—CH₃ | 128–130° C. |
| 22 | B7 | —NH—CO—C₃H₇ | >200° C. |
| 23 | B1 | —NH₂ | 94–97° C. |
| 24 | B1 | —NH—CH₃ | 178–180° C. |
| 25 | B6 | —NH—CO—CH₂-(1-pipendinyl) | 175–180° C. |
| 26 | B5 | —N=CH—N(CH₃)₂ | 175–180° C. |

TABLE 4

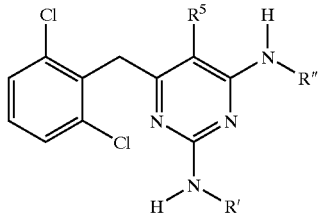

| Co. No. | Ex. No. | R' | R" | R⁵ | physical data (melting point) |
|---|---|---|---|---|---|
| 27 | B1 | 4-Br—C₆H₄ | H | H | — |
| 28 | B1 | H | 4-Br—C₆H₄ | H | — |
| 29 | B1 | 4-Cl—C₆H₄ | H | H | — |
| 30 | B1 | H | 4-Cl—C₆H₄ | H | — |
| 31 | B1 | H | (3-Br-6-pyridyl) | H | — |
| 32 | B1 | (3-Br-6-pyridyl) | H | H | — |
| 33 | B1 | 4-F—C₆H₄ | H | H | 77–80° C. |
| 34 | B1 | H | 4-F—C₆H₄ | H | >200° C. |

TABLE 4-continued

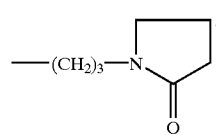

| Co. No. | Ex. No. | R' | R" | R⁵ | physical data (melting point) |
|---|---|---|---|---|---|
| 35 | B1 | 4-CH$_3$—C$_6$H$_4$ | H | H | 76–79° C. |
| 36 | B1 | H | 4-CH$_3$—C$_6$H$_4$ | H | 183–186° C. |
| 37 | B1 | C$_6$H$_5$ | H | H | 85–90° C. |
| 38 | B1 | H | C$_6$H$_5$ | H | 182–187° C. |
| 39 | B2 | —(CH$_2$)$_3$—N-pyrrolidin-2-one | 4-CN—C$_6$H$_4$ | H | 104–114° C. |
| 40 | B2 | (CH$_2$)$_2$—OH | 4-CN—C$_6$H$_4$ | H | 247–250° C.; HCl (1:1) |
| 41 | B1 | CH$_3$ | 4-CN—C$_6$H$_4$ | H | >200° C. |
| 42 | B1 | (CH$_2$)$_3$—OH | 4-CN—C$_6$H$_4$ | H | 91–105° C. |
| 43 | B2 | (CH$_2$)$_4$—OH | 4-CN—C$_6$H$_4$ | H | 161–163° C. |
| 45 | B1 | H | 4-CN—C$_6$H$_4$ | H | >200° C. |
| 46 | B1 | H | 4-CN—C$_6$H$_4$ | CH$_3$ | >200° C. |
| 47 | B1 | 4-CN—C$_6$H$_4$ | H | CH$_3$ | >200° C. |
| 48 | B1 | H | 4-Br—C$_6$H$_4$ | CH$_3$ | >200° C. |
| 49 | B1 | 4-Br—C$_6$H$_4$ | H | CH$_3$ | 168–170° C. |

TABLE 5

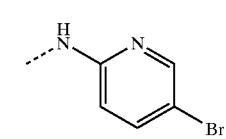

| Co. No. | Ex. No. | R' | R" | R''' | R⁵ | physical data |
|---|---|---|---|---|---|---|
| 50 | B1 | NH$_2$ | 4-CN—C$_6$H$_4$ | O-(2,6-diCl—C$_6$H$_3$) | H | >200° C. |
| 51 | B1 | CH$_2$-(2,6-diCl—C$_6$H$_3$) | H | —NH-(4-CN—C$_6$H$_4$) | H | >200 |
| 90 | B9a | NH-(2-NO$_2$-4-CN—C$_6$H$_3$) | 2,4,6-triCH$_3$—C$_6$H$_2$ | H | H | 165–168° C. |
| 91 | | NH-(3-OH-4-CN—C$_6$H$_3$) | 2,4,6-triCH$_3$—C$_6$H$_2$ | H | H | |
| 92 | B12 | NH-(2,6-diCl—C$_6$H$_3$) | 2,6-diCl—C$_6$H$_3$ | H | H | 164–166° C. |
| 93 | B9a | NH-(2,4,6-triCH$_3$—C$_6$H$_2$) | 4-CN—C$_6$H$_4$ | H | H | 267–268° C. |
| 94 | B1 | NH-(4-CN—C$_6$H$_4$) | 2,4,6-triCH$_3$—C$_6$H$_2$ | NH$_2$ | H | 263–264° C. |
| 95 | B1 | NH$_2$ | 2,4,6-triCH$_3$—C$_6$H$_2$ | —NH-(4-CN—C$_6$H$_4$) | H | 233–234° C. |
| 96 | B8a | NH-(4-Cl—C$_6$H$_4$) | 2,4,6-triCH$_3$—C$_6$H$_2$ | H | H | |
| 97 | B8a | NH-(2,4-diF—C$_6$H$_3$) | 2,4,6-triCH$_3$—C$_6$H$_2$ | H | H | |
| 98 | B8a | NH-(5-bromopyridin-2-yl) | 2,4,6-triCH$_3$—C$_6$H$_2$ | H | H | |
| 99 | B9a | NH-(2,4,6-triCH$_3$—C$_6$H$_2$) | 4-CN—C$_6$H$_4$ | H | CH$_3$ | 200–201° C. |

TABLE 5-continued

[Structure: pyrimidine with R''' at 6-position, R5 at 5-position, NHR'' at 4-position, R' at 2-position]

| Co. No. | Ex. No. | R' | R'' | R''' | R5 | physical data |
|---|---|---|---|---|---|---|
| 100 | B11 | -NH-C6H4-C(=O)NH2 (4-carbamoylphenylamino) | 2,4,6-triCH3—C6H2 | H | H | |
| 101 | B8a | -NH-C6H3(2-NH2)(4-C(=O)NH2) | 2,4,6-triCH3—C6H2 | H | H | |
| 102 | B8a | -NH-C6H3(2-NH2)(4-CN) | 2,4,6-triCH3—C6H2 | H | H | |
| 103 | B1 | -NH-C6H4-CH2-CN (4-cyanomethylphenylamino) | H | —CH2-(2,6-diCl—C6H3) | CH3 | >200° C. |
| 104 | | NH-(4-CN—C6H4) | C6H5—CH2— | H | H | |
| 105 | | NH-(2,4,6-triCH3—C6H2) | 2,4,6-triCH3—C6H2 | H | H | |

TABLE 6

[Structure: phenyl ring with R6a, R6b, R6c, R6d substituents, linked via X to pyrimidine (R5 at 5-position) with NH-C6H4-CN at 2-position]

| Co. No. | Ex. No. | X | R5 | R6a | R6b | R6c | R6d | physical data (salt form; melting point) |
|---|---|---|---|---|---|---|---|---|
| 52 | B8a | NH | H | CH3 | H | CH3 | CH3 | 217–218° C. |
| 53 | B11 | NH | H | CH3 | H | CH3 | CH3 | HCl (1:1) |
| 54 | B11 | NH | H | CH3 | H | CH3 | CH3 | HBr (1:1) |
| 55 | B11 | NH | H | CH3 | H | CH3 | CH3 | L-tartrate |
| 56 | B9a | NH | H | CH3 | H | Br | CH3 | HCl (1:1); 214–217° C. |
| 57 | B9a | NH | H | CH3 | H | H | CH3 | HCl (1:1); >270° C. |
| 58 | B10 | O | H | CH3 | H | CH3 | CH3 | 220–222° C. |

TABLE 6-continued

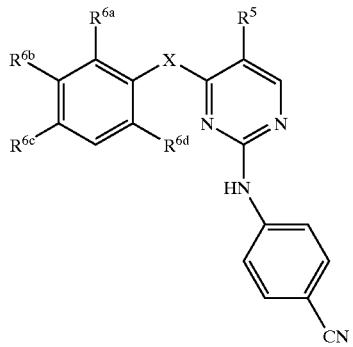

| Co. No. | Ex. No. | X | $R^5$ | $R^{6a}$ | $R^{6b}$ | $R^{6c}$ | $R^{6d}$ | physical data (salt form; melting point) |
|---|---|---|---|---|---|---|---|---|
| 59 | B10 | S | H | Cl | H | H | Cl | 225–226° C. |
| 60 | B3 | O | H | Cl | H | Cl | Cl | 279–280° C. |
| 61 | B9a | NH | H | Br | H | $CH_3$ | Br | 230–233° C. |
| 62 | B9a | NH | H | Br | H | $CH(CH_3)_2$ | Br | 198–200° C. |
| 63 | B3 | NH | $CH_3$ | $CH_3$ | H | $CH_3$ | $CH_3$ | 236–237° C. |
| 64 | B10 | O | H | Cl | H | Cl | $CH_3$ | 266–267° C. |
| 65 | B9a | NH | H | Cl | H | H | Cl | 253–255° C. |
| 66 | B9c | NH | H | Cl | H | $CF_3$ | Cl | 239–240° C. |
| 67 | B9c | NH | H | Br | H | F | Cl | 244–245° C. |
| 68 | B9a | NH | H | Cl | H | Cl | $CH_3$ | 217° C. |
| 69 | B8b or B9a | NH | H | $CH_3$ | H | CN | $CH_3$ | 225–230° C. |
| 70 | B9c | NH | H | Br | H | Br | F | 210–214° C. |
| 71 | B9c | $N(CH_3)$ | H | $CH_3$ | H | $CH_3$ | $CH_3$ | 218–219° C. |
| 72 | B9c | NH | H | Cl | H | Cl | Cl | trifluoroacetate (1:1); 225–230° C. |
| 73 | B10 | S | H | $CH_3$ | H | $CH_3$ | $CH_3$ | 204.5–208° C. |
| 74 | B10 | O | H | Br | H | Cl | $CH_3$ | 246–249° C. |
| 75 | B9c | NH | H | $CH_3$ | H | Cl | $CH_3$ | 206–207° C. |
| 76 | B9a | NH | H | Cl | H | CN | Cl | >180° C. |
| 77 | B9c | NH | H | Cl | H | $OCF_3$ | Cl | 185–190° C. |
| 78 | B9c | NH | H | Br | Cl | Br | Cl | >265° C. |
| 79 | B9c | NH | H | Br | H | $C_3H_7$ | Br | 215–218° C. |
| 80 | B9a | NH | H | $CH_3$ | H | $C(CH_3)_3$ | $CH_3$ | 203–205° C. |
| 81 | B10 | O | H | $CH_3$ | H | CN | $CH_3$ | 279–980° C. |
| 82 | B9c | NH | $CH_3$ | $CH_3$ | H | Cl | $CH_3$ | 235–937° C. |
| 83 | B9b | NH | $CH_3$ | $CH_3$ | H | CN | $CH_3$ | $H_2O$ (1:1) trifluoroacetate (1:1); 274–275° C. |
| 84 | B9c | NH | $CH_3$ | $CH_3$ | H | $C(CH_3)_3$ | $CH_3$ | 231–232° C. |
| 85 | B9c | NH | $CH_3$ | $CH_3$ | H | Br | $CH_3$ | 218–219° C. |
| 86 | B9c | S | $CH_3$ | $CH_3$ | H | $CH_3$ | $CH_3$ | 229–230° C. |
| 87 | B9a | NH | $CH_3$ | Br | H | $C_3H_7$ | Br | 197–198° C. |
| 88 | B9a | NH | $CH_3$ | Br | H | $CH(CH_3)_2$ | Br | 157–158° C. |
| 89 | B9b | NH | $CH_3$ | $CH_3$ | H | CN | $CH_3$ | >300° C. |

C. Pharmacological Example

Example C.1

A rapid, sensitive and automated assay procedure was used for the in vitro evaluation of anti-HIV agents. An HIV-1 transformed T4-cell line. MT-4, which was previously shown (Koyanagi et al., *Int. J. Cancer*, 36, 445–451, 1985) to be highly susceptible to an permissive for HIV infection, served as the target cell line. Inhibition of the HIV-induced cytopathic effect was used as the end point. The viability of both HIV- and mock-infected cells was assessed spectrophotometrically via the in situ reduction of 3-(4,5-dimethylthiazol-2-yl)-2,5-diphenyltetrazolium bromide (MIU). The 50% cytotoxic concentration ($CC_{50}$ in $\mu$M) was defined as the concentration of compound that reduced the absorbance of the mock-infected control sample by 50%. The percent protection achieved by the compound in HIV-infected cells was calculated by the following formula:

$$\frac{(OD_T)_{HIV} - (OD_C)_{HIV}}{(OD_C)_{MOCK} - (OD_C)_{HIV}} \text{ expressed in \%,}$$

whereby $(OD_T)_{HIV}$ is the optical density measured with a given concentration of the test compound in HIV-infected cells: $(OD_C)_{HIV}$ is the optical density measured for the control untreated HIV-infected cells: $(OD_C)_{MOCK}$ is the optical density measured for the control untreated mock-infected cells: all optical density values were determined at 540 nm. The dose achieving 50% protection according to the above formula was defined as the 50% inhibitory concentration ($IC_{50}$ in $\mu$M). The ratio of $CC_{50}$ to $IC_{50}$ was defined as the selectivity index (SI). The compounds of formula (I) were shown to inhibit HIV-1 effectively. Particular $IC_{50}$, $CC_{50}$ and SI values are listed in Table 7 hereinbelow.

TABLE 7

| Co. No. | IC$_{50}$ ($\mu$M) | CC$_{50}$ ($\mu$M) | SI |
|---|---|---|---|
| 1 | 0.027 | 49.7 | 1860 |
| 2 | 0.035 | >100 | >2890 |
| 3 | 0.016 | 37.4 | 2558 |
| 4 | 0.315 | >100 | >317 |
| 5 | 0.094 | 56.2 | 598 |
| 6 | 0.020 | 24.4 | 1192 |
| 7 | 0.975 | >100 | >102 |
| 8 | 8.147 | >100 | >12 |
| 9 | 0.037 | 58.6 | 1587 |
| 10 | 2.529 | >100 | >39 |
| 12 | 1.683 | 55.1 | 32 |
| 13 | 0.005 | 7.8 | 1557 |
| 14 | 2.183 | 89.0 | 40 |
| 15 | 0.003 | 9.0 | 2857 |
| 16 | 0.389 | 41.2 | 105 |
| 17 | 0.167 | 9.1 | 54 |
| 18 | 2.1 | 59.9 | 29 |
| 19 | 0.006 | 53.6 | 8642 |
| 20 | 0.026 | 36.5 | 1413 |
| 21 | 0.017 | 50.6 | 2910 |
| 22 | 0.035 | 12.2 | 346 |
| 23 | 0.001 | 47.9 | 59935 |
| 24 | 0.020 | 54.0 | 2667 |
| 25 | 0.079 | >100 | >1272 |
| 26 | 0.011 | 33.5 | 2990 |
| 27 | 0.017 | >20 | >1169 |
| 28 | 0.079 | >20 | >253 |
| 29 | 0.015 | >20 | >1324 |
| 30 | 0.088 | >20 | >228 |
| 31 | 0.024 | 86.8 | 3630 |
| 32 | 0.403 | >100 | >248 |
| 33 | 0.042 | 43.4 | 1038 |
| 34 | 0.319 | 57.8 | 181 |
| 35 | 0.103 | 42.3 | 409 |
| 36 | 0.323 | >100 | >309 |
| 37 | 0.443 | 33.4 | 75 |
| 38 | 2.449 | 32.4 | 13 |
| 39 | 1.531 | >100 | >65 |
| 40 | 0.253 | 40.2 | 158 |
| 41 | 1.986 | 34.2 | 17 |
| 42 | 0.352 | 35.5 | 88 |
| 43 | 0.603 | >100 | >165 |
| 45 | 0.010 | 56.3 | 5688 |
| 46 | 45.2 | >100 | >2 |
| 47 | 0.004 | >100 | >27027 |
| 48 | 44.2 | >100 | >1 |
| 49 | 0.058 | 45.2 | 786 |
| 50 | 0.518 | 52.0 | 100 |
| 51 | 0.452 | >100 | >221 |
| 52 | 0.001 | 2.08 | 2314 |
| 53 | 0.0006 | 1.3 | 2111 |
| 56 | 0.0023 | 1.9 | 839 |
| 57 | 0.0007 | 0.8 | 1153 |
| 58 | 0.0029 | >100 | >34482 |
| 59 | 0.0012 | >100 | >83333 |
| 60 | 0.29 | >100 | >350 |
| 61 | 0.0007 | 0.1 | 155 |
| 62 | 0.0032 | 8.7 | 2716 |
| 63 | 0.0017 | 0.3 | 198 |
| 64 | 0.12 | >100 | >840 |
| 65 | 0.18 | 0.2 | 1 |
| 66 | 0.0085 | 19.9 | 2347 |
| 67 | 0.0024 | 0.4 | 152 |
| 68 | 0.001 | 1.4 | 1367 |
| 69 | 0.0004 | 4.7 | 11632 |
| 70 | 0.0006 | 5.8 | 9641 |
| 71 | 0.0063 | 45.8 | 7275 |
| 72 | 0.0007 | 0.5 | 705 |
| 73 | 0.0036 | >100 | >27777 |
| 74 | 0.010 | >100 | >9523 |
| 75 | 0.0021 | 1.9 | 911 |
| 76 | 0.0033 | 5.2 | 1580 |
| 77 | 0.0030 | 9.6 | 3188 |
| 78 | 0.0028 | 0.4 | 144 |
| 79 | 0.0031 | 4.8 | 1547 |
| 80 | 0.011 | 8.7 | 771 |
| 81 | 0.0011 | >100 | >90909 |
| 82 | 0.0026 | 0.4 | 151 |
| 83 | 0.0008 | 0.4 | 541 |
| 84 | 0.012 | 9.3 | 753 |
| 85 | 0.002 | 0.4 | 208 |
| 86 | 0.010 | >100 | >9803 |
| 87 | 0.0031 | 2.2 | 711 |
| 88 | 0.0027 | 2.1 | 767 |
| 89 | 0.0007 | 0.4 | 619 |
| 90 | 3.4 | 30.8 | 9 |
| 91 | 0.0025 | 4.9 | 1976 |
| 92 | 45.0 | >90.0 | >2 |
| 93 | 0.0035 | 48.1 | 13743 |
| 94 | 0.0022 | 11.1 | 5064 |
| 95 | 0.0006 | 7.7 | 12783 |
| 96 | 0.0031 | 5.8 | 1885 |
| 97 | 0.032 | 13.2 | 415 |
| 98 | 2.0 | 13.8 | 7 |
| 99 | 0.16 | 59.7 | 367 |
| 100 | 0.075 | 0.8 | 10 |
| 101 | 0.053 | 29.5 | 558 |
| 102 | 0.0082 | 0.5 | 63 |
| 103 | 0.022 | >100 | 4555 |
| 104 | 0.0034 | 18.6 | 5476 |
| 105 | 52.1 | <52.1 | <1 |

D. Composition Examples

The following formulations exemplify typical pharmaceutical compositions suitable for systemic administration to animal and human subjects in accordance with the present invention.

"Active ingredient" (A.I.) as used throughout these examples relates to a compound of formula (I) or a pharmaceutically acceptable addition salt thereof.

Example D.1

Film-Coated Tablets

Preparation of Tablet Core

A mixture of 100 g of the A.I., 570 g lactose and 200 g starch was mixed well and thereafter humidified with a solution of 5 g sodium dodecyl sulfate and 10 g polyvinylpyrrolidone in about 200 ml of water. The wet powder mixture was sieved, dried and sieved again. Then there was added 100 g microcrystalline cellulose and 15 g hydrogenated vegetable oil. The whole was mixed well and compressed into tablets, giving 10.000 tablets, each comprising 10 mg of the active ingredient.

Coating

To a solution of 10 g methyl cellulose in 75 ml of denaturated ethanol there was added a solution of 5 g of ethyl cellulose in 150 ml of dichloromethane. Then there were added 75 ml of dichloromethane and 2.5 ml 1,2,3-propanetriol, 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated color suspension and the whole was homogenated. The tablet cores were coated with the thus obtained mixture in a coating apparatus.

What is claimed is:
1. A compound of formula (II'-B)

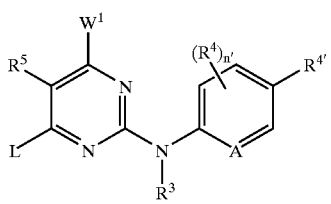

(II'-B)

wherein R$^3$ is hydrogen, aryl, C$_{1-6}$alkylcarbonyl, C$_{1-6}$alkyl, C$_{1-6}$alkyloxycarbonyl, C$_{1-6}$alkyl substituted with C$_{1-6}$alkyloxycarbonyl and each R$^4$ independently is hydroxy, halo, C$_{1-6}$alkyl, C$_{1-6}$alkyloxy, cyano, aminocarbonyl, nitro, amino, trihalomethyl, trihalomethyloxy or C$_{1-6}$alkyl substituted with cyano or aminocarbonyl;

R$^5$ is hydrogen or C$_{1-4}$alkyl;

R$^{4'}$ is cyano, aminocarbonyl, or C$_{1-6}$alkyl substituted with cyano or aminocarbonyl;

n' is 0, 1, 2 or 3;

A is CH, CR$^4$ or N;

L is C$_{1-10}$alkyl substituted with one or two substituents independently selected from C$_{3-7}$cycloalkyl, indanyl, indolyl and phenyl, wherein said phenyl, indanyl and indolyl may be substituted with one, two, three, four or where possible five substituents each independently selected from halo, hydroxy, C$_{1-6}$alkyl, C$_{1-6}$alkyloxy, cyano, aminocarbonyl, C$_{1-6}$alkyloxycarbonyl, formyl, nitro, amino, trihalomethyl, trihalomethyloxy and C$_{1-6}$alkylcarbonyl, or L is —X$^1$—R$^6$ wherein X$^1$ is —NR$^3$—, or —O— and R$^6$ is 2,4,6-trichlorophenyl, 2,4,6-trimethyl-phenyl, 2,4-dibromo-3,5-dichloro-phenyl, 2,4-dibromo-6-fluoro-phenyl, 2,4-dichloro-6-methyl-phenyl, 2,6-dibromo-4-isopropyl-phenyl, 2,6dibromo-4-methylphenyl, 2,6-dibromo-4-prop-1-yl-phenyl, 2,6-dichloro-4-cyano-phenyl, 2,6-dichloro-4-trifluoromethoxy-phenyl, 2,6-dichloro-4-trifluoromethyl-phenyl, 2,6-dichloro-phenyl, 2,6-dimethyl-4-(1,1-dimethylethyl)-phenyl, 2,6-dimethyl-phenyl, 2-bromo-4-fluoro-6-methyl-phenyl, 2-bromo-6-chloro-4-fluoro-phenyl, 4-bromo-2,6-dimethyl-phenyl, 4-chloro-2,6-dimethyl-phenyl, 4-cyano-2,6-dimethyl-phenyl; or L is —X$^2$-Alk-R$^7$ wherein
R$^7$ is phenyl or phenyl substituted with one, two, three, four or five substituents each independently selected from halo, hydroxy, C$_{1-6}$alkyl, C$_{1-6}$alkyloxy, C$_{1-6}$alkylcarbonyl, C$_{1-6}$alkyloxycarbonyl, formyl, cyano, aminocarbonyl, nitro, amino, trihalomethyloxy and trihalomethyl; and
X$^2$ is —NR$^3$—, —NH—NH—, —N=N—, —O—, —S—, —S(=O)— or —S(=O)$_2$—; Alk is C$_{1-4}$alkanediyl;

aryl is phenyl or phenyl substituted with one, two, three, four or five substituents each independently selected from halo, C$_{1-6}$alkyl, C$_{1-6}$alkyloxy, cyano, nitro and trifluoromethyl;

and W$^1$ is a halogen.

* * * * *